(12) United States Patent
Nash et al.

(10) Patent No.: US 7,534,249 B2
(45) Date of Patent: *May 19, 2009

(54) SYSTEM AND METHOD OF USE FOR AGENT DELIVERY AND REVASCULARIZING OF GRAFTS AND VESSELS

(75) Inventors: John E. Nash, Chester Springs, PA (US); William T. Fisher, Schwenksville, PA (US); Charles W. Dodson, Jr., King of Prussia, PA (US)

(73) Assignee: Kensey Nash Corporation, Exton, PA (US)

( * ) Notice: Subject to any disclaimer, the term of this patent is extended or adjusted under 35 U.S.C. 154(b) by 921 days.

This patent is subject to a terminal disclaimer.

(21) Appl. No.: 10/665,337

(22) Filed: Sep. 18, 2003

(65) Prior Publication Data

US 2004/0097995 A1 May 20, 2004

Related U.S. Application Data

(63) Continuation of application No. 10/121,192, filed on Apr. 12, 2002, now Pat. No. 6,905,505, which is a continuation of application No. 09/594,131, filed on Jun. 14, 2000, now Pat. No. 6,524,323, which is a continuation of application No. 09/233,712, filed on Jan. 19, 1999, now Pat. No. 6,080,170, which is a continuation-in-part of application No. 08/900,598, filed on Jul. 25, 1997, now Pat. No. 5,879,361, which is a continuation-in-part of application No. 08/690,438, filed on Jul. 26, 1996, now Pat. No. 5,779,721.

(51) Int. Cl.
*A61B 17/22* (2006.01)

(52) U.S. Cl. .................................... 606/159
(58) Field of Classification Search ............... 606/159, 606/170, 174, 180

See application file for complete search history.

(56) References Cited

U.S. PATENT DOCUMENTS 4,445,509 A 5/1984 Auth (Continued)

FOREIGN PATENT DOCUMENTS

EP 0353087 1/1990

(Continued)

OTHER PUBLICATIONS

Kolodgie et al, Local delivery of ceramide for restenosis: is there a future for lipid therapy?, Circulation Res., Aug. 18, 2000.

(Continued)

*Primary Examiner*—Kevin T Truong
(74) *Attorney, Agent, or Firm*—Law office of Jeffrey R. Ramberg

(57) ABSTRACT

A system and method for opening a lumen in an occluded blood vessel, e.g., a coronary bypass graft, of a living being. The system comprises an atherectomy catheter having a working head, e.g., a rotary impacting impeller, and a debris extraction sub-system. The atherectomy catheter is located within a guide catheter. The working head is arranged to operate on, e.g., impact, the occlusive material in the occluded vessel to open a lumen therein, whereupon some debris may be produced. The debris extraction sub-system introduces an infusate liquid at a first flow rate adjacent the working head and withdraws that liquid and some blood at a second and higher flow rate, through the guide catheter to create a differential flow adjacent the working head, whereupon the debris is withdrawn in the infusate liquid and blood for collection outside the being's body. The introduction of the infusate liquid may also be used to establish an unbalanced flow adjacent the working head to enable the atherectomy catheter to be steered hydrodynamically. A guide wire having an inflatable balloon on its distal end may be used with the atherectomy catheter to block the flow of debris distally, while enabling distal tissues to be perfused with an oxygenating liquid. At least one flow control port may be provided in the guide catheter to prevent collapse of the vessel being revascularized. A cradle is provided to fix the guide catheter and guide wire in position within the body of the being while enabling the atherectomy catheter to be advanced along the guide wire and through the guide catheter.

87 Claims, 16 Drawing Sheets

U.S. PATENT DOCUMENTS

| | | |
|---|---|---|
| 4,589,412 A | 5/1986 | Kensey |
| 4,631,052 A | 12/1986 | Kensey |
| 4,679,558 A | 7/1987 | Kensey et al. |
| 4,686,982 A | 8/1987 | Nash |
| 4,696,667 A | 9/1987 | Masch |
| 4,700,705 A | 10/1987 | Kensey et al. |
| 4,747,821 A | 5/1988 | Kensey et al. |
| 4,749,376 A | 6/1988 | Kensey et al. |
| 4,762,129 A | 8/1988 | Bonzel |
| 4,775,371 A | 10/1988 | Mueller, Jr. |
| 4,790,813 A | 12/1988 | Kensey |
| 4,842,579 A | 6/1989 | Shiber |
| 4,857,045 A | 8/1989 | Rydell |
| 4,883,458 A | 11/1989 | Shiber |
| 4,898,575 A | 2/1990 | Fischell et al. |
| 4,957,482 A | 9/1990 | Shiber |
| 5,009,659 A | 4/1991 | Hamlin et al. |
| 5,022,553 A | 6/1991 | Pontius |
| 5,030,201 A | 7/1991 | Palestrant |
| 5,042,984 A | 8/1991 | Kensey et al. |
| 5,047,040 A | 9/1991 | Simpson et al. |
| 5,049,124 A | 9/1991 | Bales, Jr. |
| 5,074,841 A | 12/1991 | Ademovic |
| 5,087,265 A | 2/1992 | Summers |
| 5,097,849 A | 3/1992 | Kensey et al. |
| 5,114,399 A | 5/1992 | Kovalcheck |
| 5,120,308 A | 6/1992 | Hess |
| 5,135,483 A | 8/1992 | Wagner et al. |
| 5,195,956 A | 3/1993 | Stockmeier |
| 5,209,727 A | 5/1993 | Radish, Jr. et al. |
| 5,224,945 A | 7/1993 | Pannek, Jr. |
| 5,267,955 A | 12/1993 | Hanson |
| 5,273,526 A | 12/1993 | Dance et al. |
| 5,282,484 A | 2/1994 | Reger |
| 5,284,486 A | 2/1994 | Kotula et al. |
| 5,314,407 A | 5/1994 | Auth et al. |
| 5,358,472 A | 10/1994 | Vance et al. |
| 5,366,463 A | 11/1994 | Ryan |
| 5,368,603 A | 11/1994 | Halliburton |
| 5,370,609 A | 12/1994 | Drasler et al. |
| 5,370,651 A | 12/1994 | Summers |
| 5,385,152 A | 1/1995 | Abele et al. |
| 5,395,311 A | 3/1995 | Andrews |
| 5,402,790 A | 4/1995 | Jang et al. |
| 5,409,454 A | 4/1995 | Fischell et al. |
| 5,423,742 A | 6/1995 | Theron |
| 5,429,136 A | 7/1995 | Milo et al. |
| 5,462,529 A | 10/1995 | Simpson et al. |
| 5,496,267 A | 3/1996 | Drasler et al. |
| 5,632,755 A | 5/1997 | Nordgren et al. |
| 5,665,098 A | 9/1997 | Kelly et al. |
| 5,665,103 A | 9/1997 | Lafontaine et al. |
| 5,679,558 A | 10/1997 | Gobel et al. |
| 5,681,336 A | 10/1997 | Clement et al. |
| 5,779,721 A | 7/1998 | Nash |
| 5,833,650 A | 11/1998 | Imran |
| 5,836,892 A | 11/1998 | Lorenzo |
| 5,868,767 A | 2/1999 | Farley et al. |
| 5,879,361 A | 3/1999 | Nash |
| 5,882,329 A | 3/1999 | Patterson et al. |
| 5,900,246 A | 5/1999 | Lambert |
| 5,947,985 A | 9/1999 | Imran |
| 5,954,745 A | 9/1999 | Gertler et al. |
| 5,976,153 A | 11/1999 | Fischell et al. |
| 6,017,319 A | 1/2000 | Jacobsen et al. |
| 6,074,407 A | 6/2000 | Levine et al. |
| 6,080,170 A | 6/2000 | Nash et al. |
| 6,093,157 A | 7/2000 | Chandrasekaran |
| 6,126,667 A | 10/2000 | Barry et al. |
| 6,135,991 A | 10/2000 | Muni et al. |
| 6,217,567 B1 | 4/2001 | Zadno-Azizi et al. |
| 6,235,042 B1 | 5/2001 | Katzman |
| 6,264,672 B1 | 7/2001 | Fisher |
| 6,296,616 B1 | 10/2001 | McMahon |
| 6,319,244 B2 | 11/2001 | Suresh et al. |
| 6,344,049 B1 | 2/2002 | Levinson et al. |
| 6,436,056 B1 | 8/2002 | Wang et al. |
| 6,482,217 B1 | 11/2002 | Pintor et al. |
| 6,544,276 B1 | 4/2003 | Azizi |
| 6,652,480 B1 | 11/2003 | Imran et al. |

FOREIGN PATENT DOCUMENTS

| | | |
|---|---|---|
| EP | 0806212 | 11/1997 |
| WO | WO 92/21386 | 12/1992 |
| WO | WO 93/00119 | 1/1993 |
| WO | WO 95/21576 | 8/1995 |
| WO | WO 98/04199 | 2/1998 |
| WO | WO 99/21510 | 5/1999 |
| WO | WO 00/54659 | 9/2000 |
| WO | WO 00/67647 | 11/2000 |
| WO | WO 01/10313 | 2/2001 |

OTHER PUBLICATIONS

Charles et al., Ceramide-coated balloon catheters limit neoinitmal hyperlasia after stretch injury in carotid arteries, Circulation Res., Aug. 18, 2000, 87:287.

Bonan, Local drug delivery for the treatment of thrombus and restenosis, J. of Invasive Cardiology, Oct. 1996, 8:399-408.

Rotoblator; Heart Technology, Inc.

Extraction Atherectomy, Putting Plaque and Thrombus in their Proper Place; Interventional Technologies, Inc.

AngioJet Rapid Thrombectomy System; Possis Medical Inc. Innovations for Life; May 1996.

Rheolytic Thrombectomy System AngioJet; Possis Medical, Inc. Innovations for Life.

Amplatz Thrombectomy Device, The Clot-Buster; Microvena Corporation.

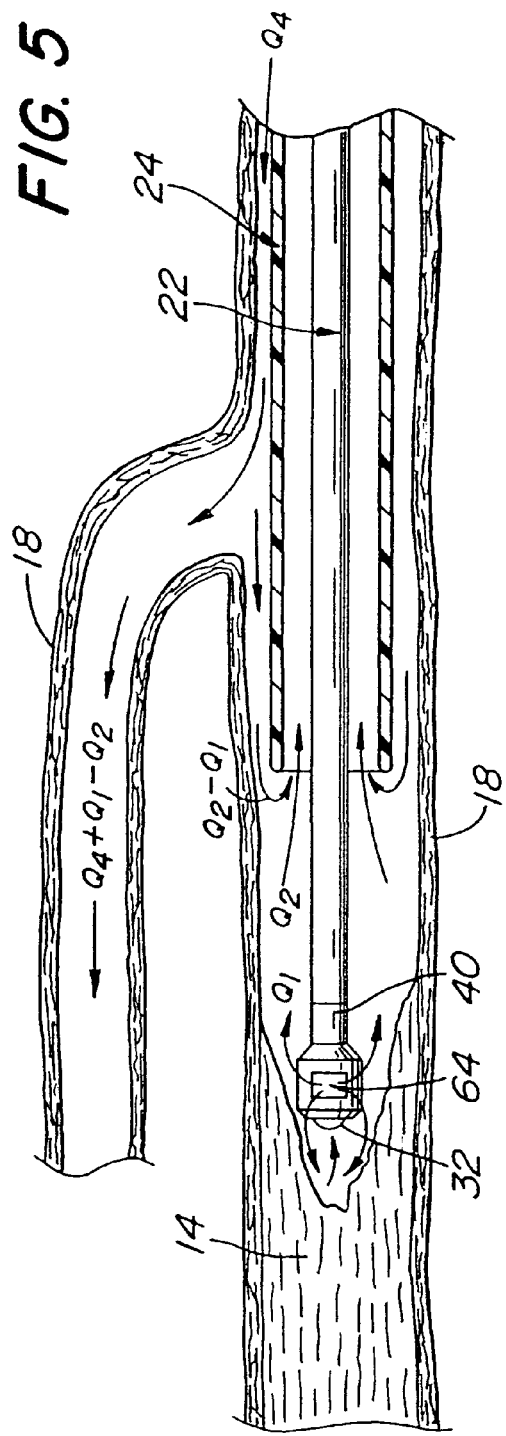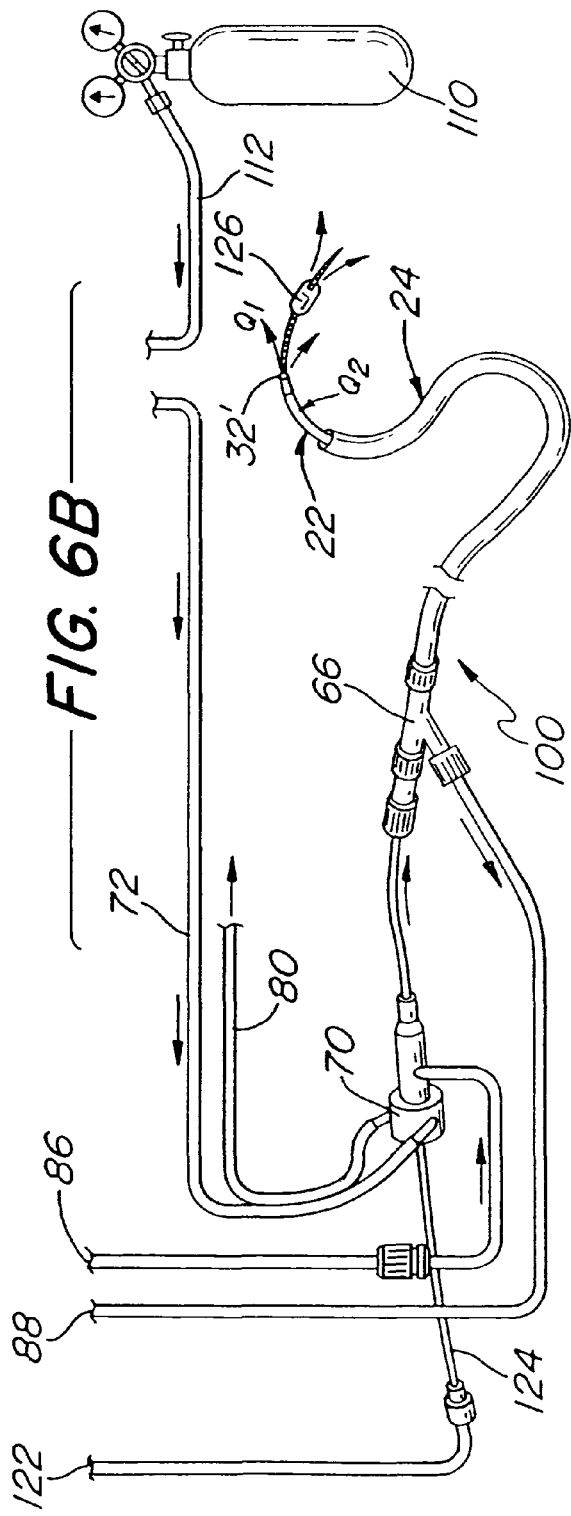

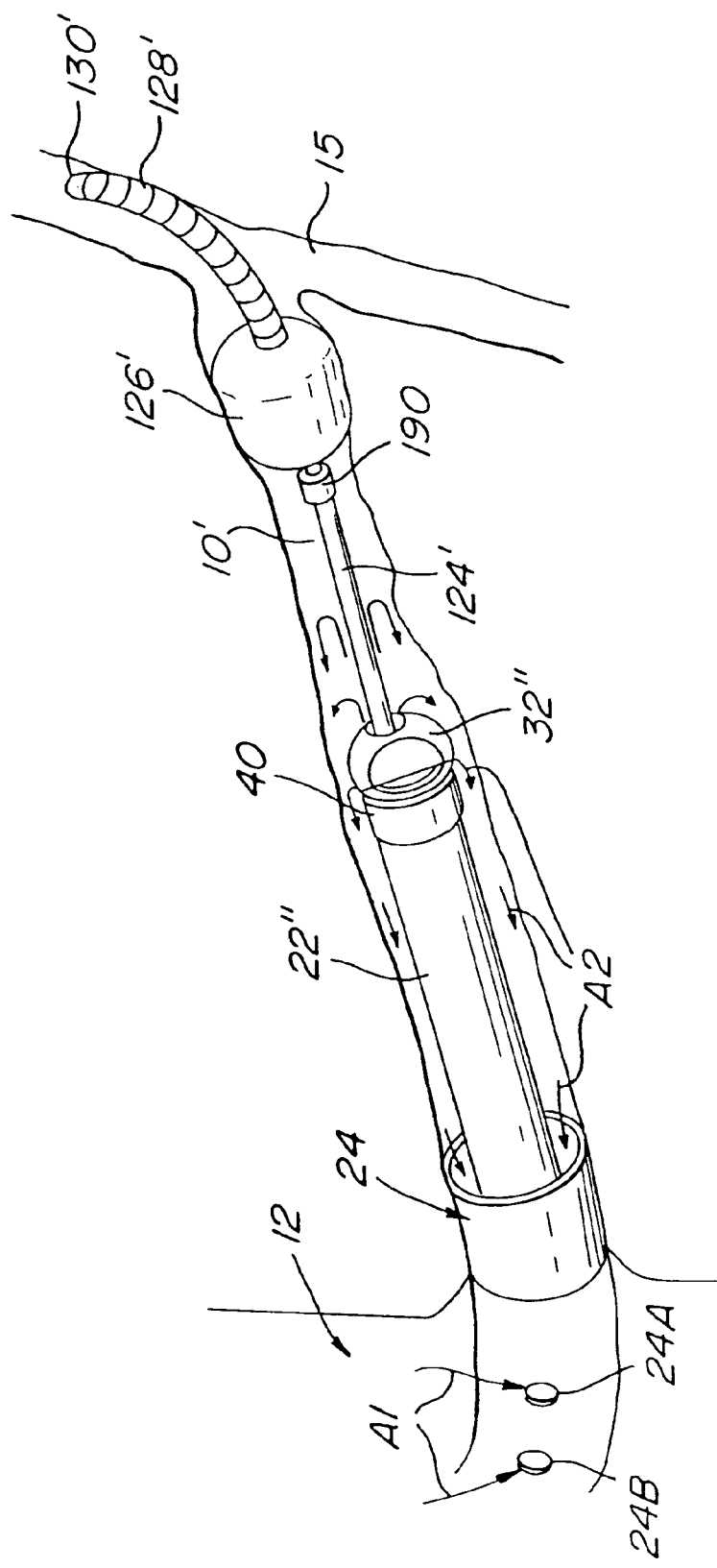

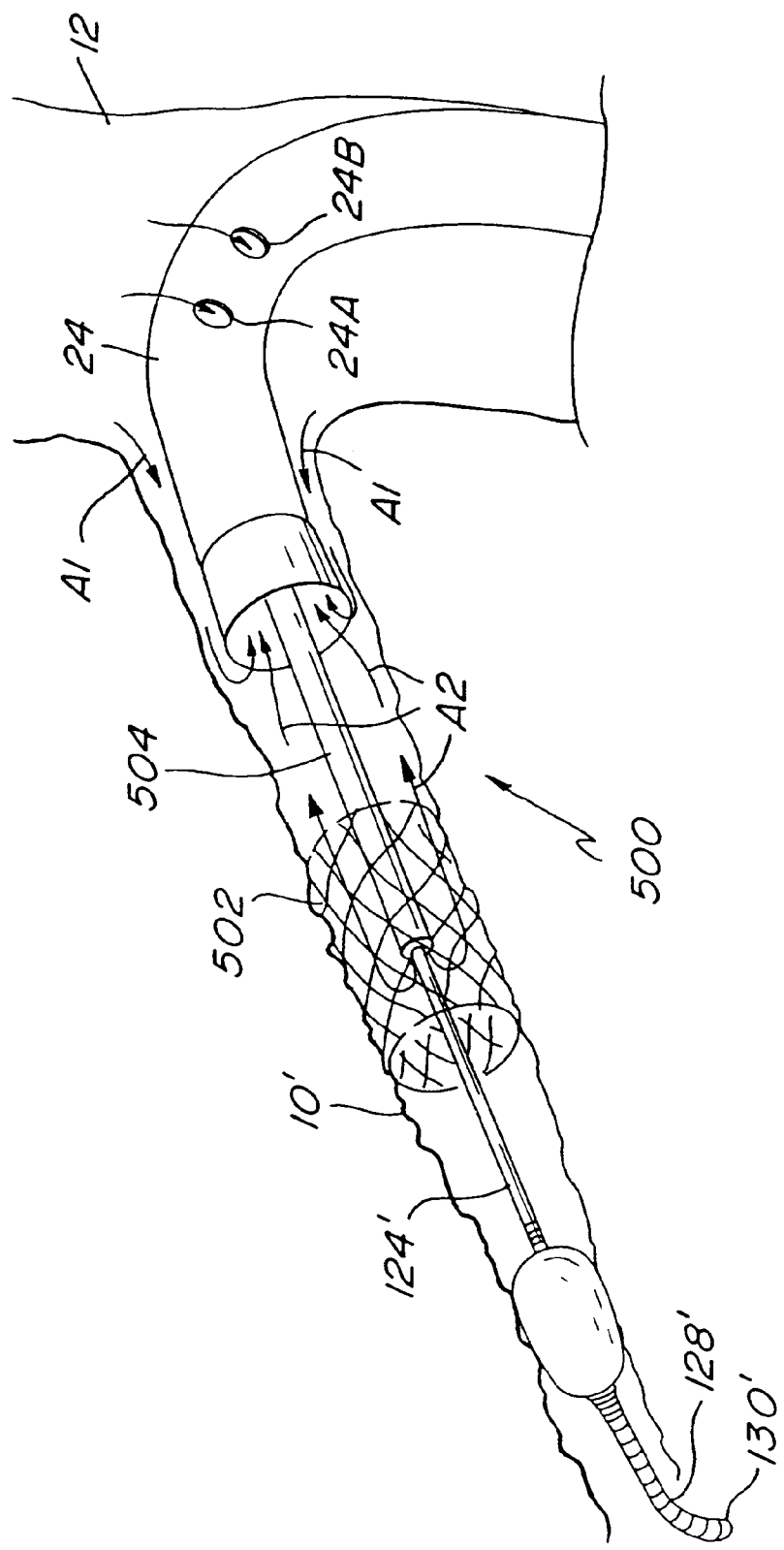

SYSTEM AND METHOD OF USE FOR AGENT DELIVERY AND REVASCULARIZING OF GRAFTS AND VESSELS

RELATED APPLICATION

This application is a Continuation of application Ser. No. 10/121,192, filed Apr. 12, 2002 now U.S. Pat. No. 6,905,505, entitled System and Method of Use for Agent Delivery and Revascularizing of Grafts and Vessels, which is a Continuation of application Ser. No. 09/594,131, filed on Jun. 14, 2000 now U.S. Pat. No. 6,524,323, entitled System and Method of Use for Revascularizing Stenotic Bypass Grafts and Other Occluded Blood Vessels, which is a Continuation of U.S. patent application Ser. No. 09/233,712, filed on Jan. 19, 1999, entitled System And Method Of Use For Revascularizing Stenotic Bypass Grafts and Other Occluded Blood Vessels, now U.S. Pat. No. 6,080,170, which is a Continuation-In-Part of U.S. patent application Ser. No. 08/900,598, filed on Jul. 25, 1997, entitled System And Method Of Use For Revascularizing Stenotic Bypass Grafts And Other Blood Vessels, now U.S. Pat. No. 5,879,361, which in turn is a Continuation-In-Part of U.S. application Ser. No. 08/690,438, filed on Jul. 26, 1996, entitled System And Method Of Use For Revascularizing Stenotic Bypass Grafts And Other Blood Vessels, now U.S. Pat. No. 5,779,721, all of which are assigned to the same assignee as this invention, and whose disclosures are incorporated by reference herein.

BACKGROUND OF THE INVENTION

This application relates generally to medical instruments and methods of use to remove occlusive material from a vessel, duct or lumen within the body of a living being.

Catheter instruments have been suggested or disclosed in the patent literature for effecting non-invasive or minimally invasive revascularization of occluded arteries. For example, in U.S. Pat. No. 4,445,509 there is disclosed a recanalization catheter designed specifically for cutting away hard, abnormal deposits, such as atherosclerotic plaque, from the inside of an artery, while supposedly preserving the soft arterial tissue. That recanalizing catheter includes a sharp-edged, multi-fluted, rotating cutting tip mounted at the distal end of the catheter and arranged to be rotated by a flexible drive shaft extending down the center of the catheter. The rotation of the cutting head is stated as producing a "differential cutting" effect, whereupon relatively hard deposits are cut away from relatively soft tissue. Suction ports are provided to pull the hard particles produced by the cutting action into the catheter for removal at the proximal end thereof so that such particles do not flow distally of the catheter where they could have an adverse effect on the patients' body.

In U.S. Pat. No. 4,700,705, which is assigned to the same assignee as this invention and whose disclosure is incorporated by reference herein, there are disclosed and claimed catheters and methods of use for effecting the opening of a vessel, duct or lumen, such as the opening of a atherosclerotic restriction (partial or total occlusion) in an artery. These catheters are elongated flexible members of sufficient flexibility to enable them to be readily passed through the body of the patient to the situs of the atherosclerotic plaque in the artery to be opened. A working head is mounted at the distal end of the catheter and is arranged for high-speed rotation about the longitudinal axis of the catheter. In some embodiments the catheter may eject fluid at the working head to expedite the restriction-opening procedure.

In U.S. Pat. No. 4,747,821, which is also assigned to the same assignee as this invention and whose disclosure is incorporated by reference herein, there is disclosed and claimed other catheters particularly suited for revascularization of arteries. Each of those catheters includes a rotary working head having at least one non-sharp impacting surface to effect material removal without cutting. Moreover, those catheters are arranged to eject fluid adjacent the working head to expedite the revascularization procedure. In particular, the rotation of the working head produces a powerful, toroidal shaped vortex contiguous with the working head which has the effect of recirculating any particles that may have been broken off from the material forming the arterial restriction so that the working head repeatedly impacts those particles to reduce their size.

In U.S. Pat. No. 5,042,984, which is also assigned to the same assignee as this invention and whose disclosure is incorporated by reference herein, there are disclosed and claimed catheters whose working heads include impacting surfaces of differing aggressiveness which may be selectively brought into engagement with the restriction to be opened. Such catheters also make use of exiting jets of liquid as described above.

Other atherectomy devices for enlarging an opening in a blood vessel have been disclosed and claimed in the following U.S. Pat. No. 4,589,412 (which is assigned to the same assignee as this invention and whose disclosure is incorporated by reference herein); U.S. Pat. Nos. 4,631,052; 4,686,982 (which is assigned to the same assignee as this invention and whose disclosure is incorporated by reference herein); U.S. Pat. No. 4,749,376 (which is assigned to the same assignee as this invention and whose disclosure is incorporated by reference herein); U.S. Pat. Nos. 4,790,813; 5,009,659; 5,074,841; 5,282,484; 5,366,463; 5,368,603; 5,402,790; 5,423,742; and 5,429,136.

Some rotary atherectomy devices are in use in this country for revascularizing occluded arteries. However, their use is limited to some very selected applications. Thus, in many instances a vascular occlusion of a coronary artery can only be treated by coronary bypass surgery wherein a graft, e.g., a saphenous vein section and/or mammary artery section, is surgically shunted across the occluded coronary artery. Unfortunately a significant percentage of bypass surgical grafts become re-occluded over time. Thus, the re-occluded graft has to be either bypassed by another graft (i.e., second bypass surgery), or the re-occluded graft has to be revascularized (i.e., its lumen reopened) by some intravascular procedure. If the occluded graft is not totally occluded, balloon angioplasty may be indicated to reopen the graft. Where, however, the graft is totally occluded or heavily occluded by frangible deposits balloon angioplasty is unavailable. Thus, if revascularization of such a graft is desired, resort may be to rotary atherectomy.

One currently available rotary atherectomy device is the ROTOBLATOR.RTM. System of Heart Technology, Inc. That system utilizes a catheter having a diamond coated elliptical burr which is rotated at a high rate of speed, e.g., up to 190,000 rpm. The burr serves to break the atherosclerotic plaque into fine particles which are allowed to remain in the patient's body for disposal by the patient's reticuloendothelial system.

As is known to those skilled in the art, one problem with a rotary atherectomy device is that unless the debris produced is so small and benign that it can be left within the patient's vascular system there must be some means to ensure that the debris does not flow upstream into the aorta during the procedure or into the downstream artery graft at the break-through point when the device comes out the distal side of a total occlusion, since either action could present a significant hazard to the patient. In particular, the former route risks stroke, the later route risks local ischemia of heart muscle when debris blocks off small arteries.

Thus, the collection and/or aspiration of debris produced during the revascularization of occluded arterial bypass grafts or other blood vessels is getting considerable attention in the medical arts. For example, Possis Medical, Inc., the assignee of U.S. Pat. Nos. 5,370,609 and 5,496,267, provides catheter devices designated as the ANGIOJET Rapid Thrombolectomy System and the ANGIOJET Rheolytic Thrombolectomy System. These devices are presumably constructed in accordance with those patents and are believed to be presently undergoing clinical trials. The catheter devices disclosed in those patents utilize high velocity jets of saline to abrade the blockage. In particular, the patents disclose utilizing the momentum of the saline jets to create a local vacuum to entrain any particulate material produced by the revascularization procedure, with the momentum and the local positive pressure being sufficient to carry the saline and debris to a return collection bag.

Another atherectomy device which is currently undergoing clinical trials is the Coronary TEC.RTM. System of Interventional Technologies, Inc. That device is believed to be the subject of U.S. Pat. No. 5,224,945, and basically comprises a catheter having a working head with microtome sharp blades for cutting plaque circumferentially. The excised plaque is extracted by suction through a central lumen in the catheter into an exteriorly-located vacuum bottle. No control of the quantity of flow of the debris-carrying fluid from the catheter is disclosed.

U.S. Pat. No. 5,030,201 (Palestran) discloses a system including an expandable atherectomy catheter arranged to be rotated to cut through an occluded artery to revascularize it. The atherectomy catheter includes an expandable cutting head having plural elongated cutting members which are mounted on a flexible torque tube incorporating a vacuum or aspiration system for retrieval of excised material. The cutting head is arranged to be rotated to cause the elongated members to cut away atheromatous material or blood clots. The atherectomy catheter is arranged to be inserted into the blood vessel through a coaxial delivery catheter, also forming a part of the system. The mechanism for aspirating particles of atheromatous material or blood clots removed by the elongated cutting members is disclosed as being in the form of a vacuum port provided at the proximal end of either the delivery catheter, the atherectomy catheter or a "retracting catheter" which also constitutes a part of the system. Saline solution or some other irrigant is infused through one of the catheters of the device that is not being used for aspiration. The infusion rate of the saline solution is balanced with the aspiration rate to avoid any net removal of fluid from the vessel. In particular, the patent teaches that by balancing the infusion rate of the saline solution to the aspiration rate, the net removal of fluid from the vessel can be brought close to zero, thereby minimizing blood loss.

While the balancing of the infusion and aspiration flow rates to minimize blood loss may be desirable, such action does not insure positive removal of all debris produced during the revascularization procedure.

Accordingly, a need exists for apparatus and a method of use to revascularize partially or totally occluded blood vessels, while positively assuring that any particles produced during the revascularization procedure are removed from the patient's body. In the case of partially or totally occluded coronary bypass grafts, a need exists for intravascular atherectomy apparatus and methods of use for effectively producing a lumen through the occlusion for the free flow of blood, without the risk that any debris produced during the lumen opening procedure will enter into the aorta or downstream of the occlusion once it has been crossed or opened.

OBJECTS OF THE INVENTION

Accordingly, it is a general object of this invention to provide systems and methods which address those needs.

It is another object of this invention to provide a system and methods for effectively revascularizing partially or totally occluded blood vessels and for removing any debris produced during the procedure from the patient's body.

It is another object of this invention to provide a system and methods for safely revascularizing partially or totally occluded blood vessels.

It is still another object of this invention to provide a system and methods for effectively opening a lumen in a partially or totally occluded arterial bypass graft, without the risk of debris produced during the procedure entering the aorta or from flowing downstream once the lumen through the occlusion has been opened.

It is yet another object of this invention to provide a system and methods for effectively opening a lumen in a partially or totally occluded portion of an artery, e.g., the femoral artery, downstream of a junction with another vessel, e.g., the profunda femoris, without the risk of debris produced during the procedure entering the other vessel or from flowing downstream in the artery once the lumen through the occlusion has been opened.

It is yet a further object of this invention to provide a system and methods for revascularizing partially or totally occluded blood vessels utilizing liquid infusion and aspiration means for establishing a differential flow to positively ensure the aspiration of debris produced during the revascularization procedure.

It is yet a further object of this invention to provide a system and methods for revascularizing partially or totally occluded blood vessels utilizing liquid infusion and aspiration means which is easy to operate to effect the positive removal of debris produced during the revascularization procedure.

It is yet a further object of this invention to provide a system and methods for revascularizing partially or totally occluded blood vessels utilizing liquid infusion and aspiration means which is adjustable for effectuating the positive removal of debris produced during the revascularization procedure.

It is yet a further object of this invention to provide a system and methods for revascularizing partially or totally occluded blood vessels utilizing liquid infusion and aspiration (extraction) subsystems which effect positive removal of debris produced during the revascularization procedure but which precludes collapse of the vessel being revascularized.

SUMMARY OF THE INVENTION

These and other objects of this invention are achieved by providing a system for opening a lumen in an occluded blood vessel, e.g., a coronary bypass graft, of a living being's vascular system located downstream of another blood vessel, e.g., the aorta, from which blood will flow to the occluded blood vessel. The system basically comprises a guide catheter, a lumen-opening catheter, a debris blocking member, and a fluid flow system.

The guide catheter has a distal end portion and at least one blood entrance port located proximally of the distal end portion. The lumen-opening catheter extends through the guide catheter to establish a fluid flow passageway therebetween and has a working head, e.g., a rotatable impacting member, for location immediately adjacent the occlusive material within the occluded blood vessel portion. The working head is arranged for operating on the occlusive material, e.g., repeatedly impacting it, to open a lumen for the freer flow of blood therethrough. Some debris may be produced by the operation of the working head.

The debris blocking member is located distally of the working head to prevent debris from flowing distally thereof.

The fluid flow system is arranged to introduce an infusate liquid at a first flow rate adjacent the working head and to withdraw that liquid through the passageway between the guide catheter and the lumen opening catheter at a second and higher flow rate to create a differential flow adjacent the working head, whereupon debris produced by the operation of the working head is withdrawn by the differential flow and flows with the liquid proximally through the passageway for extraction.

The blood entrance port in the distal end portion of the guide catheter is in communication with the passageway between the guide catheter and the lumen opening catheter, whereupon blood from the patent blood vessel portion may enter for merger with the liquid and debris flowing through that passageway.

In accordance with one preferred embodiment of this invention the debris blocking member is an inflatable balloon is provided at the distal end of the instrument to physically block the egress of any debris downstream of the apparatus. Perfusion means is preferably provided to inflate the balloon and to oxygenate downstream tissue when the balloon is inflated.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 5, is an illustration showing the apparatus of FIG. 1, partially in section, during the process of revascularizing a totally occluded femoral artery downstream of the profunda femoris;

FIGS. 6A and 6B together are an illustration of another embodiment of the system of this invention for revascularizing or opening a lumen in a coronary bypass graft;

FIG. 10 is an enlarged isometric view of the distal end of the atherectomy catheter, guide catheter and guide wire of the embodiment of FIG. 9A shown during revascularization of a coronary bypass graft, where the guide catheter tightly fits within the bypass graft;

FIG. 17 is a view similar to that of FIG. 11 but showing a method of providing a stent in an occluded blood vessel section, e.g., a bypass graft, to revascularize it, and with the debris extraction system making use of a guide catheter not engaging the wall of the blood vessel section.

DETAILED DESCRIPTION OF THE PREFERRED EMBODIMENT

Figure 1:
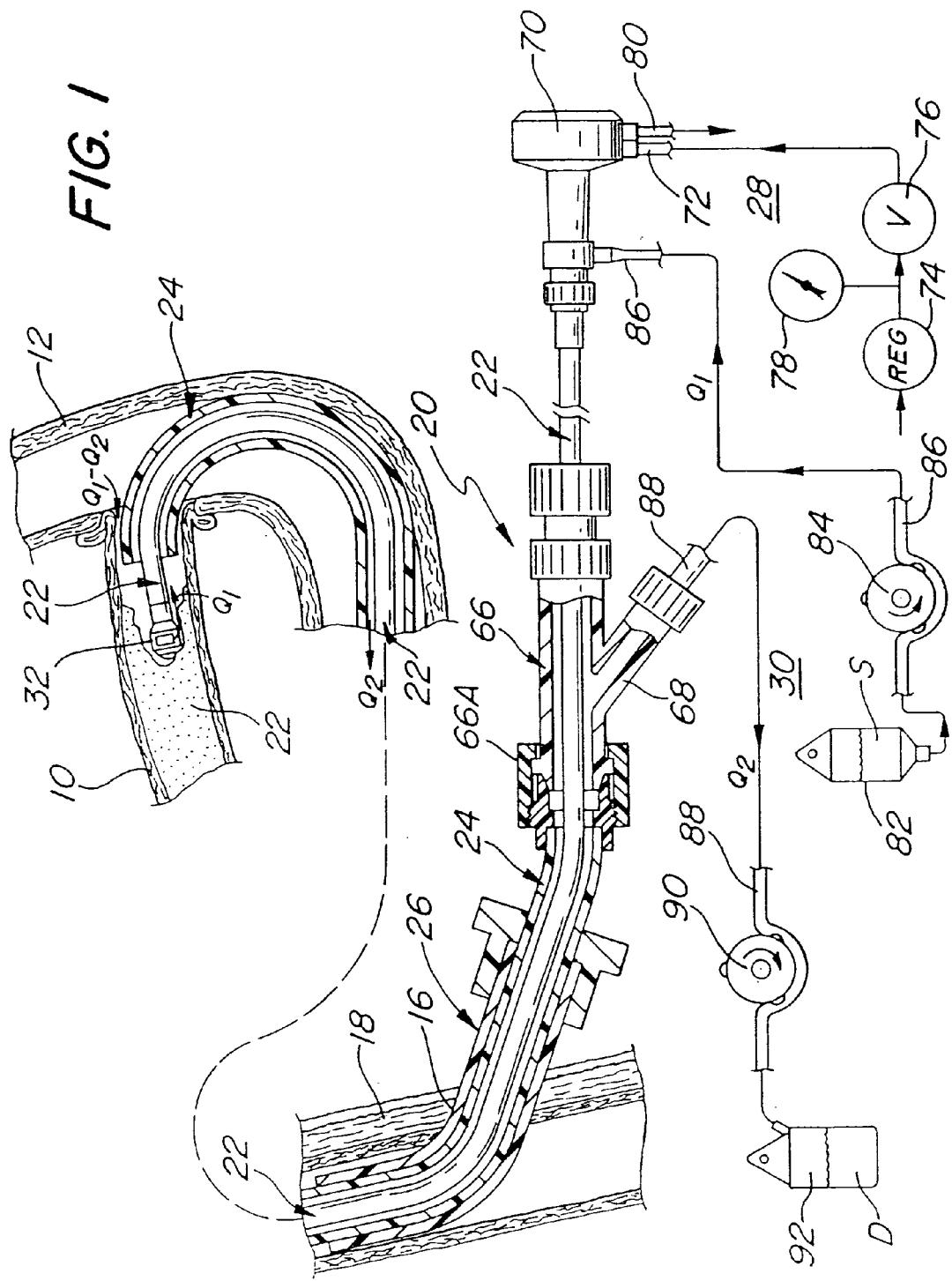
FIG. 1 is a schematic diagram, partially in section, of a system of the subject invention shown during the process of opening a lumen in a totally occluded coronary bypass graft so that blood can flow therethrough.

Referring now in greater detail to the various figures of the drawings wherein like reference characters refer to like parts, there is shown at 20 in FIG. 1 a system for revascularizing or opening a lumen through a coronary bypass graft which has become occluded, such as by the formation of a stenotic lesion or the build-up of plaque therein. As used herein the term "occluded" is given its broadest interpretation. Thus, an "occluded" graft or blood vessel may be either totally blocked or only partially blocked (i.e., there is a passageway or lumen through which some blood may flow).

The system 20 is arranged to be used for forming or enlarging a lumen through any blood vessel within the body of a living being, e.g., an occluded femoral artery downstream of the profunda femoris, not necessarily an occluded coronary bypass graft or an occluded coronary artery. In particular, the system 20 is arranged to produce a channel or lumen or to enlarge a lumen through the occlusive material within the vessel and to ensure that any particles of that material which are removed or broken away, during the revascularization procedure are prevented from flowing into the contiguous vascular system. When the system 20 is used for revascularization of occluded coronary bypass grafts, a primary application for the system 20, the debris produced is drawn into the system for extracorporeal removal and is thus prevented from entering the aorta.

As can be seen in FIG. 1, the system 20 basically comprises an "atherectomy" catheter 22, a guide catheter 24, an introducer sheath 26, a drive sub-system 28, and a debris removal sub-system 30. The atherectomy catheter 22 is in the form of an elongated flexible tubular body member or jacket at the free or distal end of which is located a rotatable working head 32. The working head 32 is generally similar to that described in U.S. Pat. No. 4,747,821. Alternatively, the working head may be constructed in accordance with the teachings of U.S. Pat. Nos. 4,679,558, 4,686,982, 4,749,376, 5,042,984, and 5,097,849, all of which are also assigned to the same assignee as this invention, and whose disclosures are also incorporated by reference herein. In fact, the working head may be any device for opening a lumen through the occlusive material.

Figure 2:
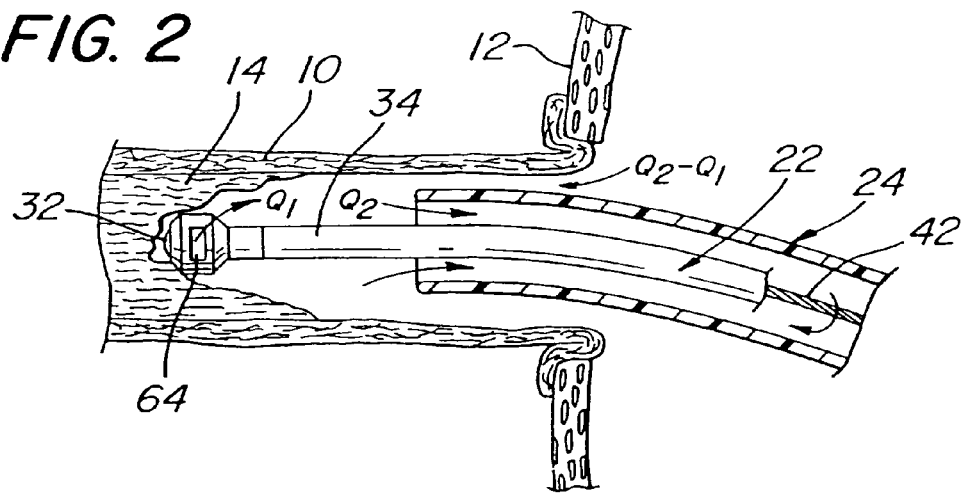
FIG. 2 is an enlarged view, partially in section, of a portion of the system of FIG. 1 shown during the process of opening a lumen in the occluded coronary bypass graft.

In use the atherectomy catheter 22 is guided through the vascular system of the patient by the guide catheter 24 (which is conventionally placed) to the site of the vascular occlusion that has been determined to exist, so that the rotary working head is located immediately adjacent the upstream end of the occlusion. In the embodiment shown in FIG. 1, the atherectomy catheter is located within a coronary bypass graft 10 having an upstream end in fluid communication with the aorta 12. The downstream end of the graft is not shown and is in fluid communication with the coronary artery being bypassed or with smaller arteries of the heart. In the example shown herein the graft 10 is totally occluded by an atherosclerotic lesion or plaque or some other occlusive material 14 (FIG. 2) within the interior of the graft.

The atherectomy catheter 22 is introduced into the patient's vascular system in a conventional manner, e.g., via the use of the introducer sheath and guide catheter. As shown, this is accomplished via a percutaneous puncture 16 in the femoral artery 18. The sheath 26 and guide catheter 24 are each of conventional construction and thus their details will not be described in the interest of brevity.

The working head 32 is arranged to rotate about the longitudinal axis of the catheter at a high rate of speed, e.g., from 10,000 rpm to 200,000 rpm to repeatedly mechanically impact the occlusive material. At the same time, an infusate liquid (to be described later) is pumped through the atherectomy catheter by a pump (to be described later and forming a portion of the debris removal sub-system 30) and out of distal end of the atherectomy catheter adjacent the working head.

The opening of the occlusion to allow freer flow of blood therethrough is effected by impacting surfaces of the rotating working head impacting the occlusive material 14, whereupon portions thereof are removed, e.g., broken away. In addition, as will be described later, the rotation of the working head produces a powerful, toroidal shaped vortex contiguous with the working head. This vortex flow has the effect of recirculating particles that are broken off from the occlusive material by the impact of the rotary working head's impacting surfaces back into contact with such surfaces. Accordingly, those particles are repeatedly impacted, with each impaction reducing the size of the particles further until the majority of resulting particle sizes are very small, e.g., less than 200 microns. At the same time another pump (also to be described later) of the debris removal sub-system 30 is operated to aspirate the particles produced during the revascularization procedure along with the infusate liquid and some blood.

Thus, as will be described in detail later, the debris removal subsystem 30 utilizing a downstream balloon, as will be described later, is operative to ensure that debris produced as the working head opens a lumen through the occlusion is not able to flow upstream into the upstream vessel, e.g., the aorta 12, during the lumen opening procedure, and once the working head breaks through or exits the occlusion on the downstream side, that the debris is not able to flow downstream into the downstream blood vessel(s).

Figure 4:
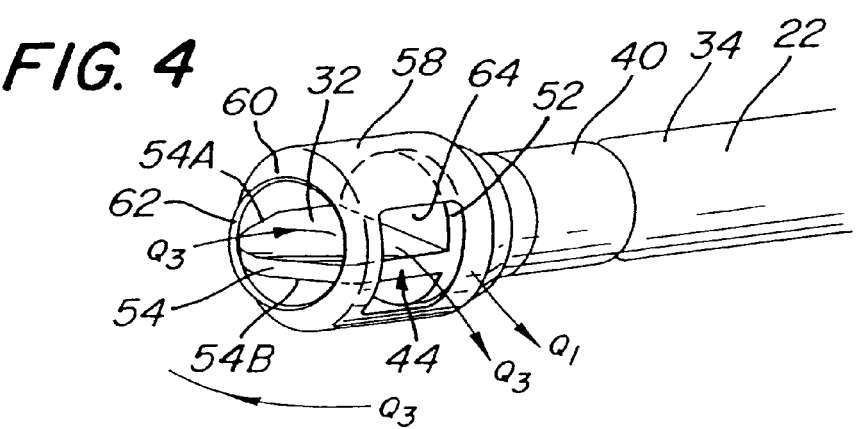
FIG. 4 is a reduced isometric view of the portion of the system shown in FIG. 3.

As best seen in FIG. 4 the atherectomy catheter includes a jacket 34 which is formed of any suitable material, e.g., plastic, and has a small outside diameter. In the preferred embodiment shown herein, the outside diameter of the jacket 34 is approximately 1.5 mm (5 French). This size catheter is merely exemplary. The means for effecting the rotation of the working head is the heretofore identified drive sub-system 28. That sub-system is similar to the drives disclosed in the aforementioned U.S. Pat. Nos. 4,686,982, and 4,747,821 and basically comprises an air-turbine motor and associated rotary drive cable (to be described later). Other drive systems can be utilized, as well.

Irrespective of the construction of the drive system, it is coupled to the working head 32 so that the working head is rotated about its longitudinal axis at the high rate of speed. Many of the details of the working head will be described later. Suffice it for now to say that the working head 32 includes an impeller portion 44 and a central shank portion or axle 36 (FIG. 4) projecting proximally therefrom. The axle 36 is supported in a central bore of a bushing 38 fixedly mounted at the distal end of the catheter's jacket 34 by an encircling mounting band 40. The shank 36 is fixedly secured to the distal end of a flexible drive cable 42 forming a portion of the drive subsystem 28.

The impeller 44 forms the distal portion of the working head and is fixedly secured to the shank 36 so that it will be rotated at a high rate of speed about its longitudinal axis by the concomitant rotation of the drive cable. The impeller portion 44 comprises a circular disk or base 52 from which a generally planar tip 54 projects. The tip 54 has a pair of generally planar diametrically disposed relieved side surfaces or faces which merge with an arcuate front or distal surface to form a pair of arcuate impacting surfaces 54A and 54B. Each of the impacting surfaces is radiused in a plane perpendicular to the axis of rotation of the working head so that each is not sharp, e.g., is in the range of approximately 0.001 inch to approximately 0.008 inch, although in the scale of the figures of the drawing they appear to be a sharp line. The working head is located within a cylindrical shroud 56 (FIGS. 3 and 4) fixedly mounted on the front of the bushing 38. The shroud 56 includes a cylindrical sidewall portion 58 and a generally conical distal wall portion 60 terminating in a circular opening 62 in the distal end thereof. The shroud maybe of any suitable outside diameter, e.g., 7 to 8 French. The distal arcuate portion of the impeller tip 54 projects out of the central or front opening 62. A side port or open window 64 is located in the sidewall 58.

As mentioned earlier the system 20 utilizes an infusate liquid to expedite the revascularization of the vessel. In particular, the infusate liquid is pumped at a flow rate $Q_1$ (to be described later) down through the interior of the catheter jacket 34 through four equidistantly spaced grooves 46 extending down the central bore of the bushing 38 and via radial ports 48 to an annular recess 50 in the front wall of the bushing. The annular recess is in fluid communication with the side port or window 64 in the shroud so that the infusate liquid can exit therefrom. The direction of flow of the infusate liquid down the atherectomy catheter and out the shroud at its working head is shown clearly in FIG. 4.

Figure 3:
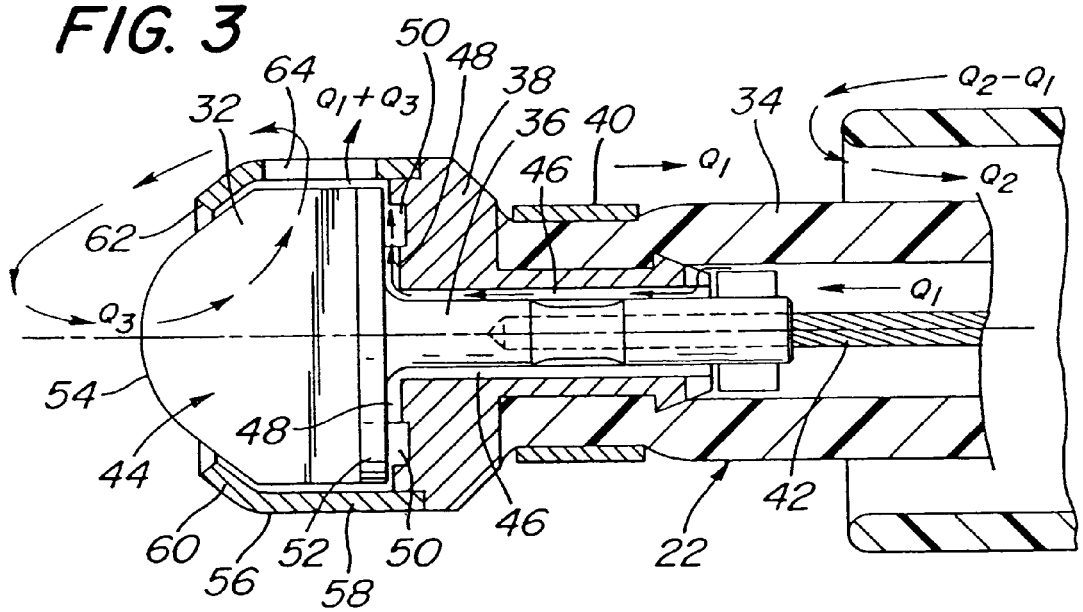
FIG. 3 is an even more greatly enlarged view, partially in section, of a portion of the system shown in FIG. 2.

The rotation of the working head about its longitudinal axis produces a powerful toroidal shaped vortex flow $Q_3$ in the fluid contiguous with the working head. This flow $Q_3$ circulates by entering into the shroud through the central or front opening 62 and exits out through the side window 64 as shown in FIG. 3. Thus, the flow exiting through window 64 is $Q_1 + Q_3$. As will be appreciated by those skilled in the art the vortex flow $Q_3$ has the effect of recirculating any particles that are broken off from the occlusive material 14 by the action of the rotating working head back into contact with the working head's impacting surfaces. Thus, the occlusive material particles which are broken away are progressively reduced in size until they are aspirated by aspiration means forming a portion of the debris removal sub-system 30. That means will be described later. Suffice it for now to state that the aspiration means withdraws the infusate liquid, the debris particles and some blood at an aspiration flow rate of $Q_2$.

As should be appreciated by those skilled in the art the liquid exiting from the window 64 of the shroud will tend to push the atherectomy catheter's distal end sideways or laterally in the direction opposite to the direction of the liquid exiting that window. This hydrodynamic action may be used to aid in steering the catheter to a desired position with respect to an occlusion to be revascularized. In this regard, for example, when negotiating a branch in the artery system to reach the occlusion to be revascularized, the atherectomy catheter can be rotated or twisted about its longitudinal axis so that the shroud's window is facing in the opposite direction to the branch to be entered. This action will cause the side directed liquid exiting the window 64 to push the catheter's distal end sideways, whereupon it can enter the desired arterial branch. Such "hydrodynamic steering" of the atherectomy catheter can be accomplished in other manners and by other means than by the use of a shroud having a single side window or port. Thus, this invention contemplates an intravascular catheter instrument, of any type, including any means for producing an asymmetric, e.g., side directed, fluid flow adjacent the distal end of the catheter so that it can be steered into a desired position by appropriate rotation of the catheter about its longitudinal axis.

As mentioned earlier, the guide catheter 24 is of any conventional construction. In the preferred embodiment shown in FIG. 1 it is a 10 F to 12 F catheter having a conventional Y connector 66 at its proximal end. The Y connector 66 has one input leg including a Touhy-Borst adjustable hemostasis valve 66A through which the atherectomy catheter 22 passes. The other input leg, i.e., the angled leg 68, is connected to the aspiration portion of the debris removal sub-system 30 (to be described later).

Power for operating the atherectomy catheter is provided by the drive sub-system 28. That system includes an air turbine motor 70 which is coupled to the proximal end of the flexible drive cable 42. The air turbine 70 is provided with compressed air via an input line or conduit 72. Air for the line 72 is provided from a source (not shown) via an associated regulator 74, and the conventional control valve 76. The control valve is coupled to the input line 72 of the air turbine. A pressure gauge 78 is connected between the regulator 74 and the control valve 76. The regulator 74, the control valve 76, the pressure gauge 78 and the associated lines or conduits and the air source make up the drive sub-system 28. The control valve 76 is of any conventional construction, be it mechanical or electrical. The air turbine motor 70 is also of any conventional construction, as is the regulator 74 and the pressure gauge 78. The air turbine includes an outlet port in communication with the ambient atmosphere, via a line 80. It must be pointed out at this juncture that the atherectomy catheter 22 need not utilize an air turbine motor to rotate the working head. For example, an electric motor can be provided to replace the air turbine to drive the rotating cable and the associated working head.

The debris removal sub-system 30 basically comprises a source 82 of the infusate liquid "S", e.g., saline plus a 30% contrast media, a first positive displacement pump 84, an input line or conduit 86, an outlet line or conduit 88, a second positive displacement pump 90, and a debris collection vessel 92. The input line 86 and its associated components, i.e., the pump 84 and infusate source 82 serve as the "infusion" means for the system 20. To that end the input line 86 is coupled via a connector to the interior of the atherectomy catheter, i.e., to the annular space within the catheter's jacket between it and the drive cable. The infusate liquid S is pumped at the flow rate $Q_1$ by the positive displacement pump 84 through line 86 from the supply or source 82. Thus, the infusate liquid S exits the catheter's working head and circulates as described earlier.

The rate of flow $Q_1$ of the infusate liquid is established by the positive displacement pump 84 under control of some automatic or manual controller (not shown). In accordance with one exemplary method of use the pump is operated to produce a flow rate $Q_1$ the range of 5-80 ml. per minute.

The output line 88 and its associated components, i.e., the pump 90 and debris collector vessel 92 serve as the "aspirating" means for the debris removal sub-system 30. To that end, the aspiration line 88 is connected to the leg 68 of the Y connector 66. The pump 90 is arranged to be operated to pump the infusate liquid, the debris produced by the revascularization, and some small amount of blood at the flow rate $Q_2$ in the proximal direction through the annular space between the atherectomy catheter 22 and the guide catheter 24 and out through the connector leg 68 into the outlet line 88, and from there to the collector vessel 92.

The flow rate $Q_2$ is selected to be greater than $Q_1$. For example, in one exemplary method of use the flow rate is selected to be in the range of 5-100 ml. per minute, with the differential between $Q_2$ and $Q_1$ being between 5 and 50 percent. The use of an aspiration flow rate $Q_2$ which is higher than the infusion flow rate $Q_1$ insures that any debris, e.g., particles of the occlusive material making up the graft's lesion, produced from debriding that material is positively prevented from flowing into adjacent vessel portions. In this regard, as will be appreciated by those skilled in the art, since the aspiration flow rate $Q_2$ is greater than the infusion flow rate $Q_1$, some blood equal to $Q_2-Q_1$ will also be withdrawn from the upstream vessel, e.g., the aorta as shown in FIGS. 1 and 3. The withdrawal of some blood from that vessel insures that the debris produced cannot flow upstream to enter into it. Instead the debris particles will be entrained within the infusate liquid and blood which is withdrawn through the aspiration line. The rate of blood withdrawn is preferably be kept to a minimum, e.g., 40 ml. per minute in the interests of patient safety.

In accordance with a preferred aspect of this invention the operation of the pumps 84 and 90 are coordinated so that $Q_2$ is equal to some variable times $Q_1$, where that variable is greater than 1 and is adjustable to accommodate the needs of the patient. Moreover, the coordination of the flow rates is preferably accomplished automatically, so that a change in one flow rate automatically results in a proportional change in the other flow rate. This coordinated action may be accomplished by a mechanical linkage between the pumps, or by a common electrical controller for the pumps. Manual control of the pumps is also envisioned for some applications.

In any case, any suitable positive displacement pumps can be utilized, e.g., peristaltic pumps or piston pumps, in the system.

In order to expedite the revascularization of the bypass graft, the infusate liquid may be provided with a contrast medium, e.g., 30% contrast medium, so that the revascularization procedure can be viewed using conventional imaging techniques. Moreover, the infusate liquid can, if desired, be oxygenated to eliminate distal ischemia when the catheter is used for arterial restriction opening procedures. Also, if desired, small amounts of heparin, urokinase, etc., or other drugs can be added to the infusate liquid for the procedure.

As should be appreciated from the foregoing the subject invention provides a viable means for effecting the revascularization of partially or totally occluded coronary bypass grafts, while assuring that any debris particles produced during the revascularization procedure is removed from the patient's body. In addition, the subject invention is suitable for revascularizing other occluded vessels, as well. For example, in FIG. 5 the system is shown in use revascularizing a totally occluded femoral artery 18 downstream of the profunda femoris 18A. In this application the system functions to capture the debris created during the lumen opening procedure by preventing it from going along side the catheter and exiting down the profunda to end up in the distal capillary beds. In this application, a portion $Q_4+Q_1-Q_2$ of the blood flowing down the femoral artery 18 to the situs of the occlusion will be permitted to flow into the profunda femoris, while the portion $Q_2-Q_1$ of the blood and infusate liquid is diverted and/or withdrawn into the guide catheter to ensure positive debris removal in the same manner as described earlier. For some persons, e.g., diabetics with severely compromised distal capillary beds, a femoral artery revascularization procedure is likely to prove beneficial.

Figure 6A:
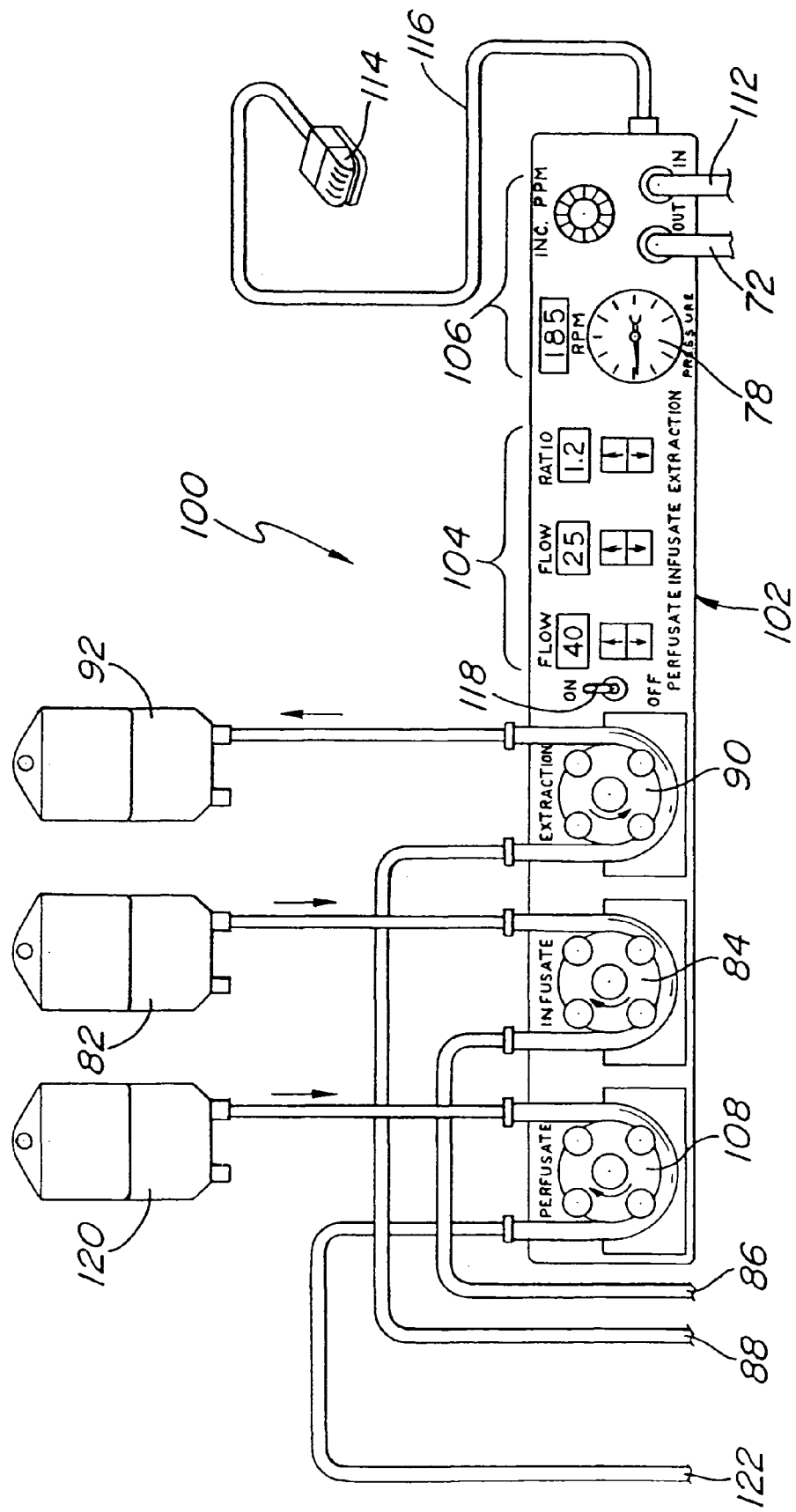

Turning now to FIGS. 6A and 6B, an alternative embodiment 100 of the system of the subject invention is shown. The system 100 is similar in most respects to system 20 described heretofore. One major difference, however, is that the atherectomy catheter is arranged for use over a guide wire (to be described later). The guide wire includes a debris blocking member, e.g., an inflatable balloon (also to be described later). When the atherectomy catheter is in place on the guide wire the balloon is located distally of the working head of the atherectomy catheter and the balloon serves to physically block any debris produced by the system 100 which may tend to escape extraction from flowing distally. The atherectomy catheter used in the system 100 is designated by the reference numeral 22' and is identical in most respects to the catheter 22 described heretofore. In the interests of brevity, the features common to catheters 22 and 22' will not be reiterated. So too, the features common to systems 100 and 20 will also not be reiterated. Moreover, in the interests of drawing simplicity common components will be given the same reference numerals.

As can be seen in FIGS. 6A and 6B, the system 100 includes a controller or console 102 housing the heretofore identified infusate pump 84 and the extraction pump 90. Each of these pumps is a peristaltic pump. The console 102 also includes a flow control section 104 for establishing the various fluid flows of the system, as will be described later, and a speed control section 106 for establishing the operational speed of the working head of the atherectomy catheter. The details of the speed control section 106 will also be described later. A perfusate pump 108 is also provided in the console 102. The perfusate pump 108 is also a peristaltic pump and its operation will be described later. Suffice it for now to state that the pump 108 is arranged to provide a perfusion liquid, e.g., blood or a suitable synthetic oxygenation liquid, downstream of the inflatable balloon to perfuse downstream (distally) located tissue. The pump 108 also serves to effect the inflation of the balloon.

Compressed gas (e.g., air or nitrogen) is provided via line 72 from the console 102 to the catheter's turbine 70. The console, in turn, receives the compressed gas from a tank 110 via an input line 112. The rotational speed of the turbine is controlled by the speed control section 106 of the console 102. On/off operation of the turbine is controlled by a turbine foot control pedal 114 and an associated gas line 116 connected to the console. This pedal also initiates operation of the infusate pump 84.

The speed control section 106 of the console includes a rotary knob for establishing the desired rotational speed of the turbine and an associated digital display for displaying the turbine's speed. The console also includes an on/off switch 118 for enabling electrical power to be provided to the system's electrical components when the switch is in the "on" position.

The foot pedal 114 is used by the operator of the system 100 to initiate operation of the infusate pump to cause the infusation liquid to flow down the guide wire and out its distal end and to start the atherectomy catheter's turbine 70 a short time, e.g., 2 seconds, after the infusate liquid begins to flow. The use of the foot pedal frees the operator's hands for other purposes.

The perfusate pump 108 is connected via an input line to a bag 120 containing the perfusion liquid. The output of the perfusate pump 108 is provided via a line 122 to the guide wire of the system 100. The guide wire is designated by the reference numeral 124 and includes the heretofore identified balloon. That balloon is designated by the reference number 126 and, as seen clearly in FIGS. 6B, 7 and 8, is located adjacent the distal end of the guide wire 124.

The atherectomy catheter 22' is an "over-the-wire" type of device. Thus, it includes a central lumen for receipt of the guide wire 124 so that the catheter 22' can be threaded over the guide wire 124. The guide wire 124 serves to perfuse distally located tissue and to inflate its balloon 126 so that the balloon blocks any particulate material (debris) from flowing distally. To accomplish these functions, the perfusate liquid in the bag 120 is pumped by the perfusate pump 108 through the line 122 and through the interior of the guide catheter 124 where some of it fills or inflates the balloon and the remainder exits at the distal end of the catheter to perfuse downstream tissue, as will be described later.

The rate of flow of the infusate, extraction and perfusate liquids is established by the flow control section 104 of the console via its various up/down switches and associated digital displays. As discussed earlier, the ratio of the infusate flow rate to the extraction flow rate is adjustable. This is accomplished by the appropriate setting of the "infusate flow" and "ratio" up/down switches of the flow control section of the console. The desired ratio and the infusate flow rate are displayed by the associated digital displays.

Figure 7:
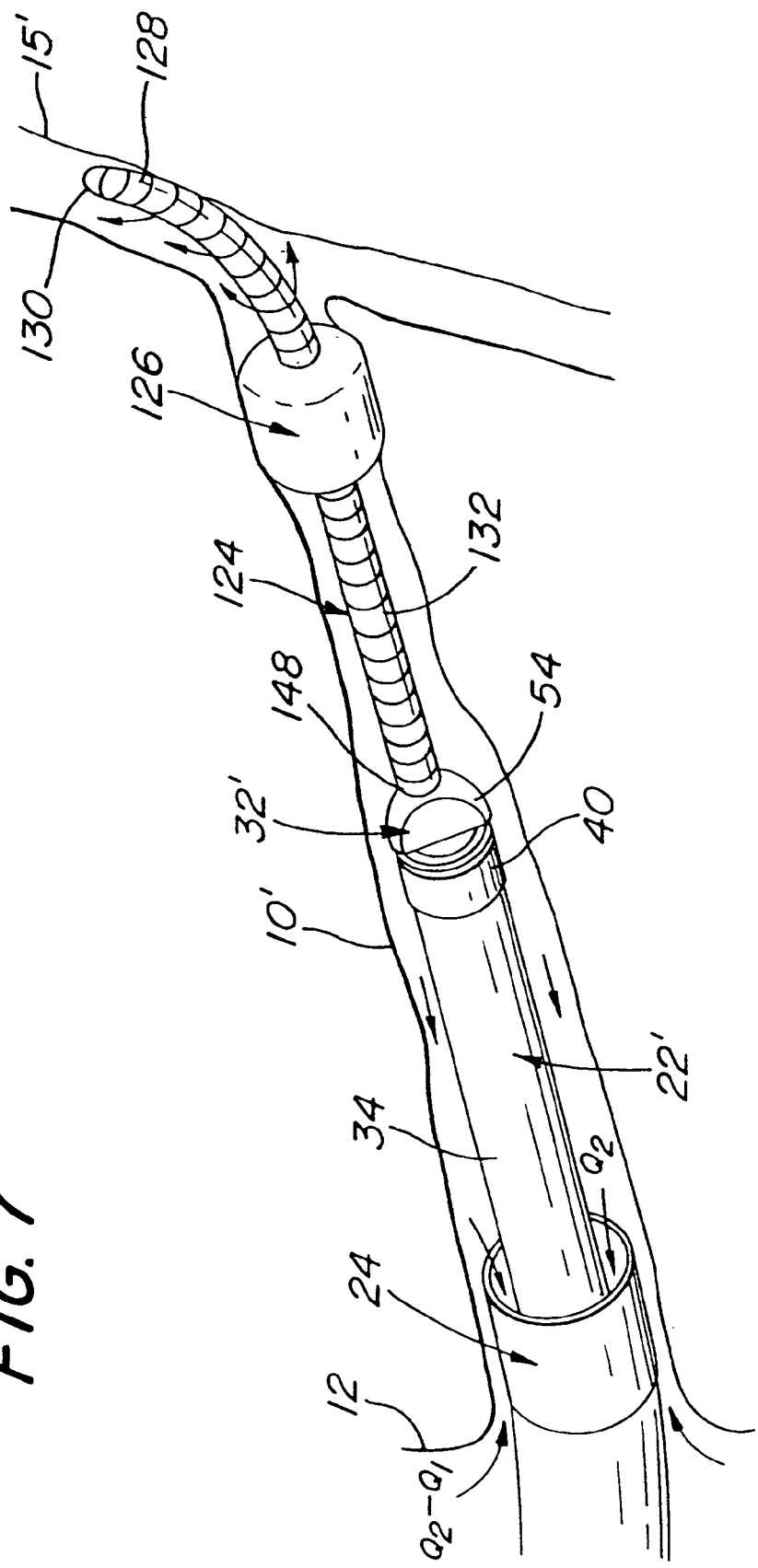
FIG. 7 is an enlarged isometric illustration of a portion of an instrument forming a component of the system shown in FIGS. 6A and 6B during the process of revascularizing a diseased bypass graft.
Figure 8:
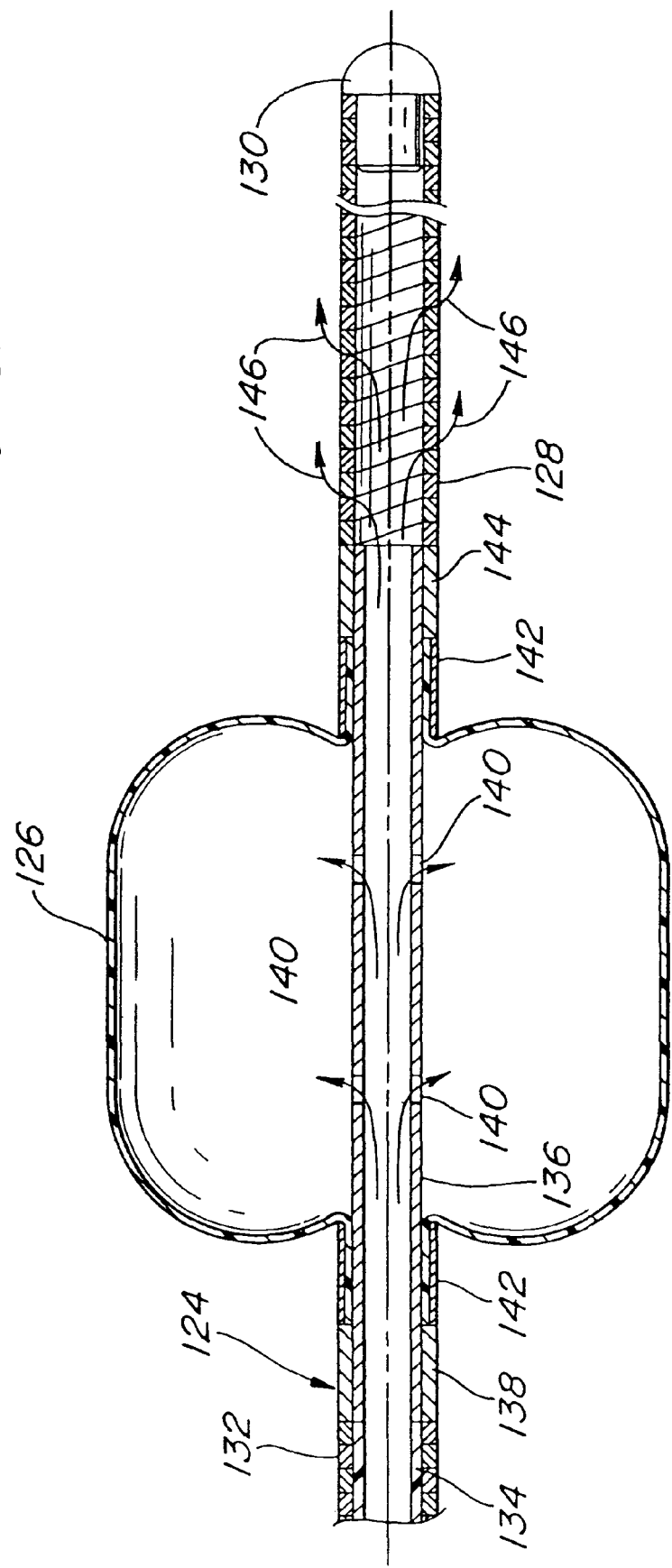
FIG. 8 is an enlarged longitudinal sectional view of the distal end of the instrument shown in FIG. 7.
Figure 9A:
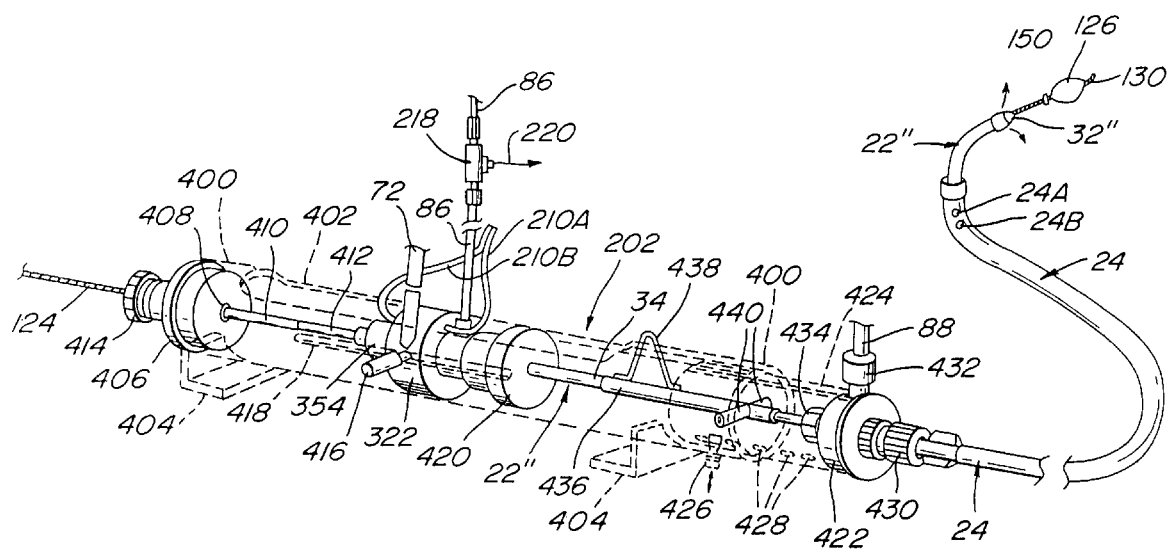
FIG. 9A is an isometric view of a portion of another preferred embodiment of this invention making use of a guide catheter having at least one flow regulation port to ensure that the vessel being revascularized does not collapse during the extraction of the debris produced by the revascularization.
Figure 9B:
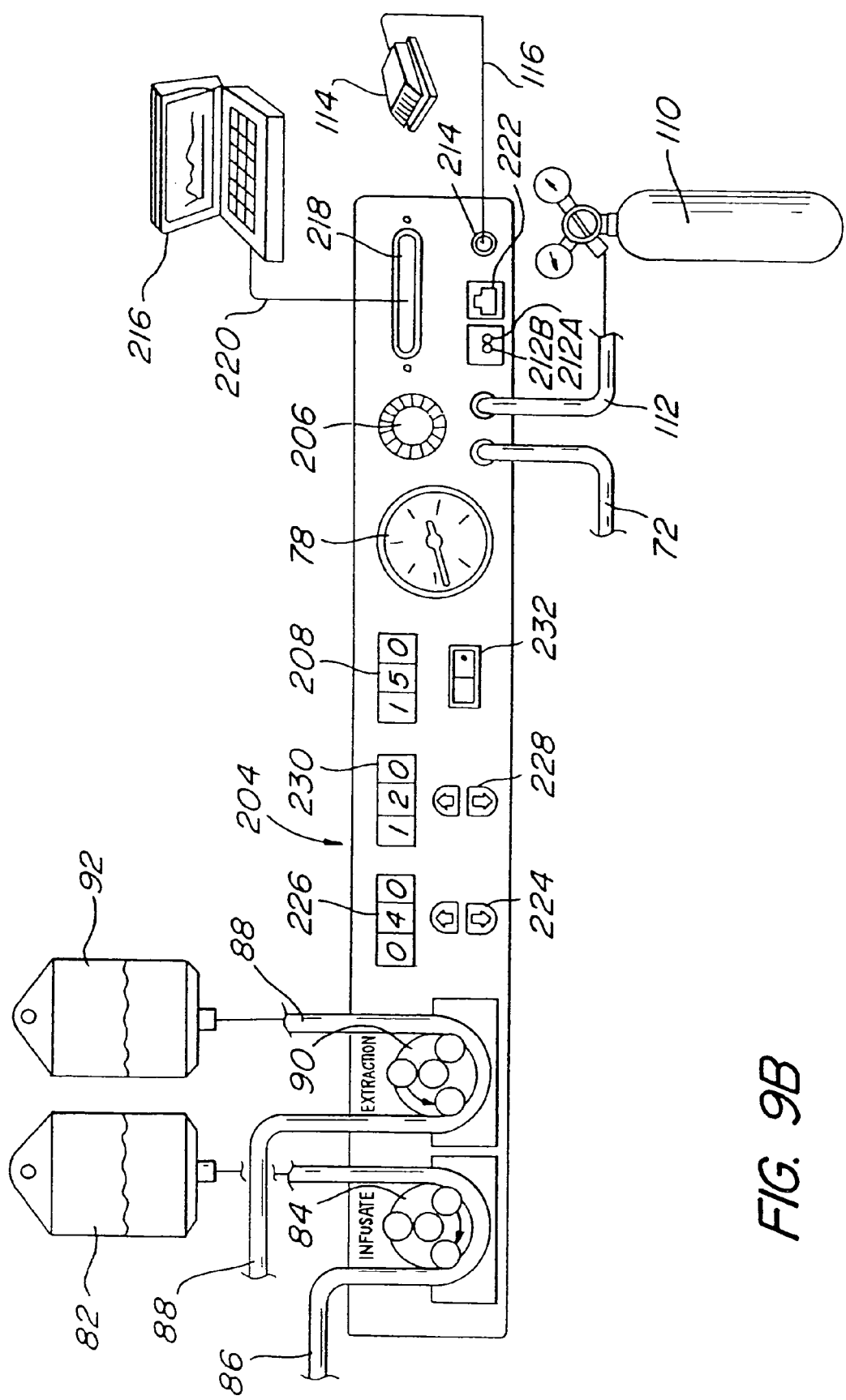
FIG. 9B is an isometric view of another portion of the embodiment of the system shown in FIG. 9.

In FIG. 7 there is shown in greater detail the distal end of the atherectomy catheter 22' located within a diseased bypass graft, e.g., a re-occluded mammary artery 10'. The diseased artery leads to a distal blood vessel 15, i.e., the vessel to be fed by the graft 10'. The guide wire 124 is in the form of an elongated flexible member, whose construction will be described later with reference to FIG. 8. The distal end of the guide wire 124 is in the form of a somewhat soft or flexible, precurved tip 128. The free end of the catheter's tip is a hemispherical dome 130. The balloon 126 is disposed slightly proximally of the free end 130 of the guide wire 124.

In FIG. 8 the details of the distal end of the guide wire 124 and balloon are shown (although the tip 128 is shown being linear in the interest of drawing simplicity). Most of the length of the guide wire, i.e, from its proximal end to the location of the balloon 126, is in the form of a two start helical spring 132 (see FIG. 8) whose convolutions are in close engagement (abutment) with one another. The spring 132 enables the guide wire to be bent through a small radius of curvature to facilitate its intravascular placement via the conventional guide catheter 24. Inside the helical spring 132 is a liquid impervious, e.g., rubber or plastic, flexible liner tube 134. This tube prevents the egress of the perfusate liquid through the interface between successive convolutions of the helical spring 132 as that liquid is pumped down the guide wire 124.

A perforated support tube 136 is mounted within a distal end helix termination 138 of the spring 132. The support tube 136 is arranged to mount the balloon 126 thereon and includes a plurality of radially located apertures or ports 140. The balloon 136 is an annular member of any conventional construction, e.g., rubber, and is mounted on and is disposed about opposite ends of the perforated support tube 136. In particular, the balloon 136 is held in place and sealed to the periphery of the support tube at each end thereof via respective bands 142. Each band 142 extends about one cylindrical end of the balloon. Thus, when the perfusion liquid is pumped down the guide wire 124 by the pump 108 it passes through the apertures or ports 140 (as shown by the arrows in FIG. 8) to fill up, i.e., inflate, the balloon 126.

The distal end of the perforated support tube is located within a spring helix termination 144 forming the proximal end of the guide wire tip portion 128. The portion 128 is also formed as a two start helix, like portion 132. However, no fluid-impervious sleeve is located within the tip portion 128 so that the interface between successive convolutions of the spring forming the tip portion 128 serve as passageways through which the portion of the perfusion liquid which doesn't enter the balloon exits the guide wire as shown by the arrows 146 in FIG. 8.

Since the atherectomy catheter 22' is designed for over-the-wire use, the drive cable for rotating its working head is in the form of a spiral spring helix having a central lumen extending down its center. The proximal end of the drive cable is connected to the output of the turbine 70 while the distal end is connected to the working head. That working head is designated by the reference number 32' and is shown in FIGS. 6A and 7. The central lumen of the spiral helix drive cable forms the passageway for receipt of the guide wire 124. If desired an anti-friction sleeve or some other anti-friction bearing can be provided at the interface between the inner surface of the spiral drive cable and the outer surface of the guide wire. The working head 32' is similar in construction to the working head 32 of system 20 except that the working head 32' includes a central bore 148 through which the guide wire 124 extends. As can be seen clearly in FIG. 7, the working head 32' is unshrouded, i.e., is not located within a shroud like the working head 32 of the atherectomy catheter 22.

Operation of the system 100 is as follows:

The guide wire 124 with its balloon 126 deflated and with the atherectomy catheter 22' mounted thereon so that the balloon 126 and tip portion 128 extend beyond the working head 32' is threaded through a preplaced guide catheter 24 in the patient's vascular system until it is at a desired situs, such as at the arch of the aorta. At this point the guide wire 124 is advanced with respect to the atherectomy catheter 22' so that the guide catheter crosses the lesion or atherosclerotic deposits in the bypass graft 10'. The precurved tip of the guide wire 124 facilitates the placement of the guide wire. In this regard, the guide wire can be rotated about its longitudinal axis to point the tip 130 in the desired direction.

Once the guide wire 124 is at the desired position, such as shown in FIG. 7, the balloon 126 can be inflated and the distally located tissue perfused. The exiting perfusion liquid is shown by the arrows in FIG. 7. In particular, the perfusate liquid is pumped by pump 108 and associated conduit 122 through the hollow interior of the guide wire 124, so that it passes through the apertures or ports 140 in the support tube 136 to inflate the balloon 126 to the state shown in FIG. 7, while the remainder of that liquid flows out of the open distal end of the support tube 136, into the hollow interior of guide wire's tip 128, and out through the interface between the immediately adjacent convolutions of the tip. Accordingly, distally located tissue is oxygenated, notwithstanding the fact that the balloon is inflated and thus blocking the flow of blood through the bypass graft 10'. If no perfusion or oxygenation of distally located tissue is desired, the system may utilize an alternative guide-wire mounted debris-blocking balloon. That alternative embodiment of the guide-wire is designated by the reference number 124', is shown clearly in FIG. 14, and will be described in detail later.

The rate of flow of the infusate liquid is set by the flow control section switch and the ratio of that flow to the extraction flow rate is established by the ratio control switch of the flow control section. Accordingly, when ready the operator presses the foot pedal 114 to start the infusate pump. This action provides the infusate liquid through line 86 and through the associated components of the catheter 22', whereupon the infusate liquid exits from the catheter at the working tip 32' as described earlier. The rate of extraction of liquid through the annular space between the inner surface of the guide catheter 24 and the outer surface of the atherectomy catheter 22' is established by the extraction pump 90 under control of the associated flow controls of the console.

The turbine 70 is arranged to commence operation on a fixed time delay, e.g., 2 seconds, after the infusate pump commences operation in response to the depression of the foot pedal 114. This action causes the working head to begin rotating at a high rate of speed. The desired speed setting for the turbine is established by setting of the rotary knob of the speed control section of the console. Preferably some restraining means (not shown but like the cradle assembly of the system 200 to be described later) is used to hold or clamp the guide wire in position when the atherectomy catheter is operated to prevent the rotation of the working head 32' from causing the guide wire to rotate. The compressed gas e.g., nitrogen or air, powering the turbine 70 of the atherectomy catheter 22' vents to the atmosphere via line 80. The debris particles produced by the rotary working head repeatedly impacting the plaque or other deposit within the diseased graft are withdrawn by the extraction pumps into the collection bag 92, in the same manner as discussed earlier. Any debris particles which may have otherwise escaped being withdrawn from the patient's body by the extraction subsystem are positively prevented from flowing distally by the barrier established by the inflated balloon 126. Thus, such particles will eventually be extracted. After the diseased bypass graft has been opened, the balloon 136 can be deflated by turning off the infusation pump. Then, the atherectomy catheter 22' and the guide wire 124 can be removed through the guide catheter 24.

It must be reiterated that the atherectomy catheter for producing the lumen through the vascular occlusion need not be a rotary impacting device, like described above. Thus, a system cons tructed in accordance with any embodiment of this invention may make use of any instrument having any type of working head, e.g., a reciprocating impacting working head, a combined rotary and reciprocating impacting working head, a rotary cutting head, a reciprocating cutting head, a rotary abrasive head, etc., to open the lumen in the occlusive material in the blood vessel. Moreover, the working head need not be shrouded. In fact, any of the heretofore identified prior art atherectomy devices can be utilized as part of the system 20 or 100. Some thrombectomy devices may also be utilized as part of the system 20 or 100 (or even as part of the systems 200 and 500, to be described later). One such potential device is the Amplatz Thrombectomy Device designated by the trademark CLOT BUSTER by Microvena Corporation. It should also be pointed out that the working head of the device for forming the lumen need not even engage the occlusive material, so long as its lumen-opening operation produces debris particles to be removed. Thus, devices making use of liquid jets, laser beams, etc., can be utilized to open the lumen as part of the system of this invention. In short, any type of instrument for opening a lumen through the occlusive material and which produces debris can benefit from use in the system of this invention, i.e., a system which establishes a differential flow, wherein the infusate flow is less than the aspiration flow so that particles or pieces of occlusive material removed are positively precluded from flowing into adjacent vessels. Moreover, while the production of a local vortex flow adjacent the working head is desirable to effectuate the lumen opening process and to reduce debris particle size, it is not crucial to this invention.

In the embodiments described in FIGS. 1-8, it has been assumed that there will be some blood flow from the patent upstream blood vessel, e.g., the aorta in the case of a revascularization of a bypass graft, which may flow about the exterior of the distal end of the guide catheter 24 to merge with the flow being drawn into the passageway between the guide catheter 24 and the atherectomy catheter 22. See for example, FIG. 7 wherein blood flow $Q_2-Q_1$ from the aorta flows around the outer surface of the distal end of the guide catheter 24 between the guide catheter and the inner wall of the bypass graft 10'. In the event that blood flow from the upstream, patent artery, e.g., the aorta 12, is precluded from entering the guide catheter 24, such as by the outer peripheral surface of the distal end of the guide catheter 24 tightly engaging the inner periphery of the bypass graft 10' to be revascularized, care must be taken to control the ingress and egress flow rates with respect to each other to ensure that the bypass graft does not collapse since the extraction or aspiration rate will exceed the infusion rate. As will be appreciated by those skilled in the art, if the bypass graft does collapse, the rotating working head 32 will be forced against the inner surface of the bypass graft wall, which is now in a flatulent state, and the risk of vascular damage will increase.

In prior art devices, such as the Clement et al. U.S. Pat. No. 5,681,336 the potential for vessel collapse is even more acute. In this regard, the Clement et al. patent positively seals off a space in the vessel to be revascularized between a pair of balloons. In particular, one balloon is located on the distal end of a guide wire distally of the restriction to be opened and the other balloon is located on the distal end of a guide catheter through which a rotary ablation catheter extends. Thus, when suction is applied to that space to evacuate the particles produced by the revascularization process, if the extraction rate is not precisely controlled and coordinated to the infusion rate, vessel collapse may occur to bring the vessel wall into the rotating burr.

The subject invention overcomes this potential vascular collapse problem. In particular, in FIGS. 9-13 there is shown another alternative embodiment of a system 200 constructed in accordance with this invention utilizing an atherectomy catheter 22" for revascularizing occluded vessels, e.g., coronary bypass grafts. The system 200 obviates the problem of potential vessel collapse by providing automatic access to blood flow from a patent, upstream vessel, e.g., the aorta 12, via use of at least one flow control or regulation port in the wall of the guide catheter 24 (or any other tubular member through which the atherectomy catheter 22" extends and through which the infusate liquid, blood and debris will be aspirated). The flow control or regulation port(s) extend(s) through the wall of the guide catheter 24 close to its distal end, yet is(are) located sufficient proximally from the distal end of the guide catheter so that when the guide catheter is in its normal position for enabling an atherectomy catheter 22" (to be described later) to revascularize the restricted vessel, e.g., a coronary bypass graft 10', the side port(s) is(are) in direct fluid communication with the blood flowing in the patent upstream vessel, e.g., the aorta 12. In the exemplary embodiment of the system 200 shown in FIGS. 9-13 two such side flow regulation ports 24A and 24B are provided near the distal end of the guide catheter 24. As will become apparent later the size, location and number of flow regulation side ports used is a matter of choice, depending upon various system parameters. For example, for a system making use of a guide catheter of 9 French (one suitable size for effecting the revascularization of coronary bypass grafts), two side ports 24A and 24B, each of 0.032 inch, may be used. Alternatively, only one side port 24A of 0.04 inch may be used. Other number(s) and sizes of side port(s) can be used as well.

Since the two side ports 24A and 24B extend through the wall of the guide catheter 24, they are in fluid communication with the interior of the guide catheter, and hence with the annular space or passageway between the inner surface of the guide catheter 24 and the outer surface of the atherectomy catheter 22" which extends through the guide catheter. As described earlier it is through this annular space or passageway that the infusate liquid, blood and any debris, e.g., atherosclerotic plaque produced by the revascularization procedure, is extracted by the extraction subsystem.

Figure 11:
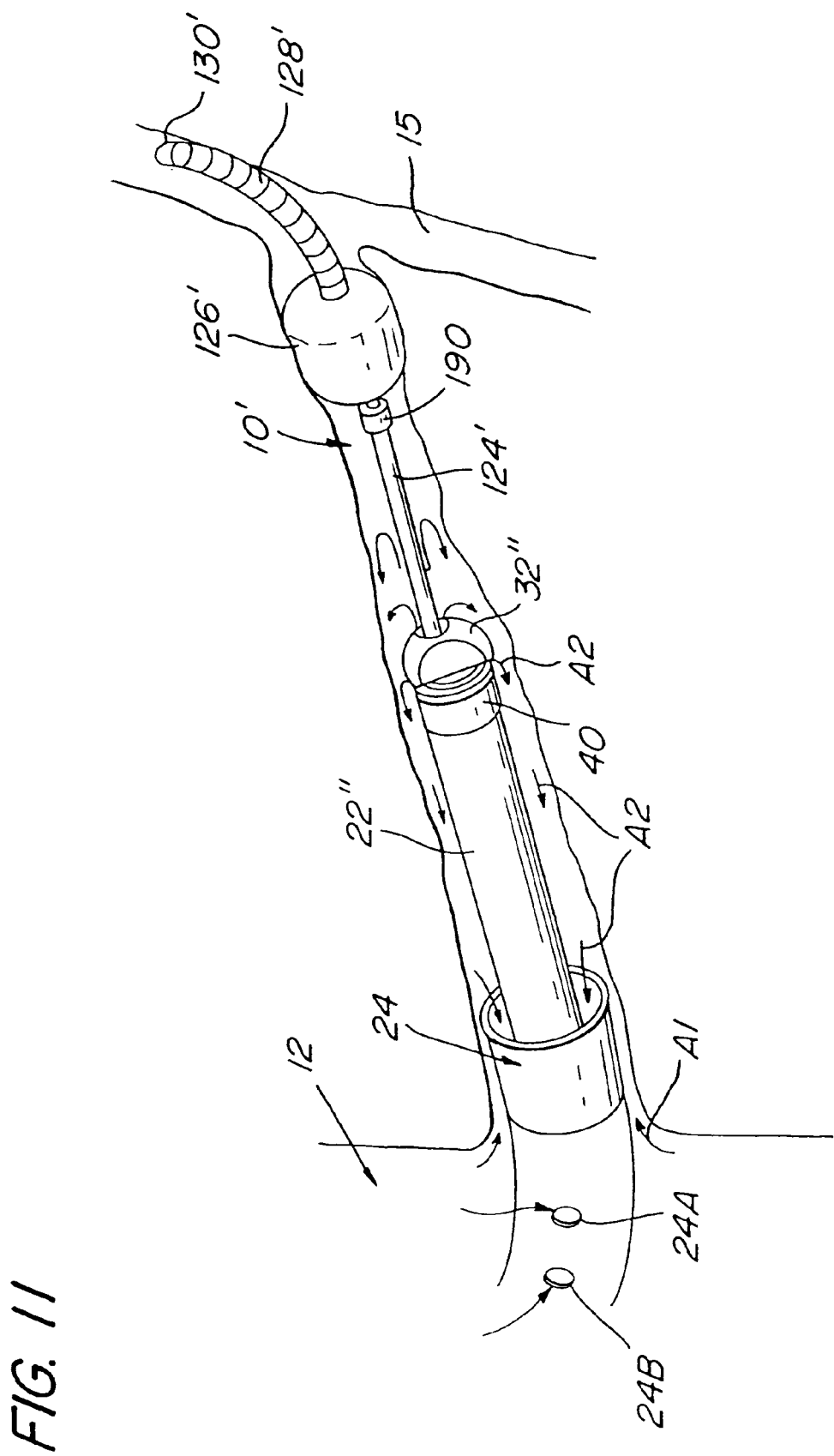
FIG. 11 is a view similar to FIG. 10 but where the guide catheter fits loosely within the bypass graft.

The use of at least one flow regulation or control port ensures that the vessel being revascularized does not collapse as the debris is extracted, even if the guide catheter 24 is tightly fit within the bypass graft 10, such as shown in FIG. 10, and even if the extraction pump 90 is operating at a much higher rate that the infusate pump 84. This automatic control or regulation provided by the at least one side port(s) will be described after a brief background discussion. To that end, as will be appreciated by those skilled in the art, if the guide catheter 24 (or other tubular member through which the atherectomy catheter extends) does not tightly fit in the bypass graft (such as shown in FIG. 11), blood from within the aorta 12 may flow around the outside of the guide catheter 24 (see the arrows A1) to join with the blood, debris particles and infusate fluid flowing into the open end of the guide catheter (see the arrows A2). Accordingly, the action of the extraction pump to remove liquid from the space in the bypass graft section between the end of the guide tube and the distally located blocking balloon 126' (forming a portion of the guidewire 124' to be described later), will not collapse that vessel section, even if the guide catheter does not make use of any flow control or regulation side port(s). If however, a guide catheter without any flow control or regulation side ports is tightly fit within the bypass graft, the possibility for vessel collapse exists if the extraction rate is not controlled precisely with respect to the infusion rate as discussed earlier.

By utilizing at least one flow control or regulation side port this potential hazard can be eliminated since such port(s) will provide automatic access to blood flow in the upstream, patent vessel. In this regard, as can be seen in FIG. 10, with the guide catheter 24 in place tightly engaging the periphery of the bypass graft section 10' blood from the aorta 12 is enabled to flow into the flow control regulation ports 24A and 24B as shown by the arrows A1. This blood then merges with the flow (shown by arrows A2) of blood, infusion liquid and debris particles produced by the action of the rotary working head 32" in the bypass graft section between the distally located blocking balloon 126' of the guide wire 124' (a variant of guide-wire 124 and which will be described later with reference to FIG. 14) and the distal end of the guide catheter 24. By appropriate sizing of the flow control side port(s) one can ensure that the pressure within the vessel being revascularized, e.g., the bypass graft, is positive, thus ensuring that the vessel section will not collapse.

The foregoing automatic flow control feature of this invention renders it useful with other revascularization systems than those of the systems disclosed herein. For example, a guide catheter 24 having at least one flow control port (or any other tubular member through which an atherectomy catheter is extended) can be used with any prior art atherectomy catheter system, e.g., the atherectomy system of the heretofore identified Clement et al. U.S. Pat. No. 5,681,336.

As discussed previously, it is desirable to operate the extraction pump at a rate to pull more fluid out of the vessel section being revascularized than the rate at which infusion liquid is introduced by the infusion pump to ensure that debris is removed even. By the use of a guide catheter 24 having at least one flow regulation port, like that described above, one can accept a significant mismatch in flow between the infusate flow and the extraction flow and still not risk collapse of the vessel being revascularized. This factor considerably simplifies the amount of coordination between the extraction pump and the infusion pump.

As mentioned earlier the size of the port or ports is a function of various system parameters. In particular, it may be calculated using the following mathematical formulae.

Pressure loss (P2−P3) through the space between the guide catheter and the working catheter is viscous and is given by the following "Equation (1)": ##EQU1## Where:

$Q1+Q2+Q3$=flow in.sup.3/sec;

D1=Guide catheter inner diameter (inches);
D2=Working catheter outer diameter (inches);
L=Guide catheter length (inches);
P2=vessel pressure (psi);
P3=vacuum source pressure (psi);
e=eccentricity factor, D1 rel. to D2.
Thus, for example, if:
L=41 inches;
D1=0.098 inches;
D2=0.067 inches
.mu.=3.25 centipoise
e=1.5 if D1 touches D2.
Then Equation (1) becomes ##EQU2##

The pressure loss through the bypass port(s) has non linear relationship to flow as set forth in the following "Equation (2)":

$Q2=90,950.0.multidot.Ab.multidot.(P1-P2).sup.0.5$

Where
Q2=flow mL/min
Ab=bypass port area in.sup.2
P1=aorta (or upstream patent vessel) pressure psi.
P2=vessel pressure psi.

Equations (1) and (2) assume that there is a tight fit between the outer surface at the distal end of the guide catheter 24 (so that blood from th e upstream, patent vessel cannot flow past the distal end of the guide catheter, as is the case shown in FIG. 7) and the total flow of blood, infusion liquid, and debris into the open end of the guide catheter is very low. Moreover, the calculations for the size of the control or regulation port(s) which follow is based on the assumption that the extraction pump 90 is not satisfied for flow and therefore has sucked or evacuated down to its limit of 27 inches of mercury, whereupon it functions as a vacuum source, rather than a flow source.

Figure 15:
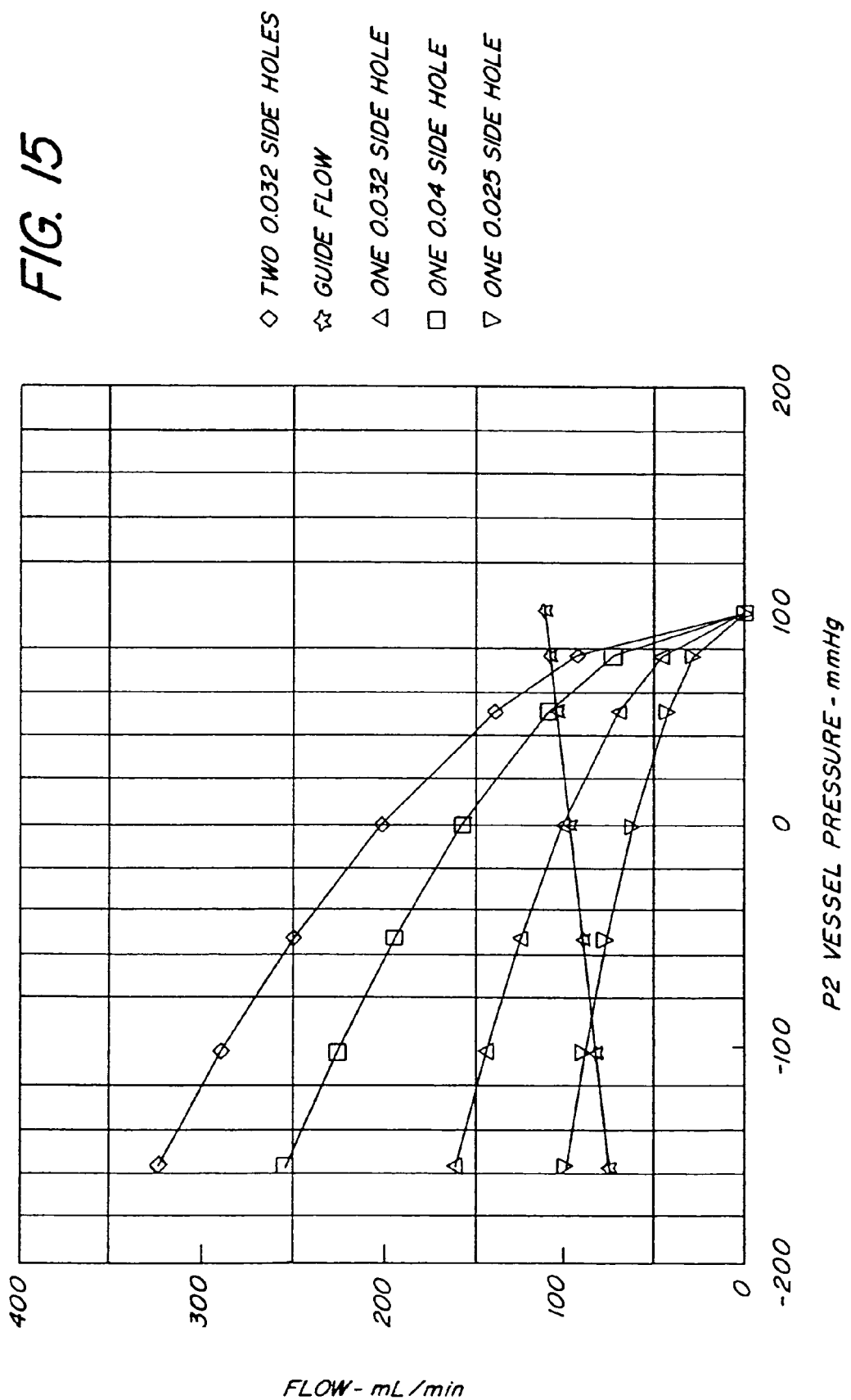
FIG. 15 is a graph showing the four potential sizes and numbers of flow regulation ports for the guide catheter and their potential for precluding collapse of the vessel being revascularized.

Equations (1) and (2) can best be solved graphically. To that end, the graph in FIG. 15 shows the solutions to pressure and flow for several sizes of flow regulation port(s) and for the guide catheter 24 using Equations (1) and (2). The intersection of the curves for the two equations represents the solution to those equations. Thus, it will be seen from the graph that the solutions for the equations with a guide catheter 24 having a pair of side ports 24A and 24B, each of 0.032 inch diameter, or a single side port 24A of 0.040 inch diameter, result in positive pressures, i.e., pressure above venous pressure. Consequently the portion of the restricted vessel, i.e., bypass graft section 10', between the distal balloon 136 and distal end of the guide catheter 24 will not collapse. However, where only one side hole or port is used and that port is either 0.032 inch diameter or of 0.025 inch diameter, a negative pressure will result in the bypass graft section 10', so that the vessel section could collapse.

It must be pointed out at this juncture that the foregoing examples are only a few of many that are possible to provide automatic protection against vessel collapse utilizing any number of side ports of various dimensions. Other factors which may be considered in the choice of number, shape and location of the at least one side port, are the desired structural integrity of the distal end of the guide catheter at the location of the side port(s), and the possibility of side port blockage by a portion of the wall of the patent upstream vessel or the wall of the vessel section being revascularized.

In FIGS. 9A, 9B, 12 and 13 there are shown the details of system 200. That system basically comprises the same system as the system 100 shown in FIGS. 6-8 described heretofore, with some slight minor modifications (as will be described later). Thus, in the interest of brevity, the common components of those systems will be given the same reference numbers and their construction and operation will not be reiterated.

The system 200 basically comprises a guide catheter 24, a modified guide wire 124' with a distally located inflatable balloon 126, an atherectomy catheter 22" with a distally located rotary working head 32" disposed over the guide wire and within the guide catheter to be moved longitudinally with respect thereto, a drive sub-system 28 for rotating the working head 32", a cradle assembly 202 (FIG. 9A) for supporting the turbine and associated portion of the drive sub-system, for fixing the position of the guide wire 124 and guide catheter 24 and for enabling the atherectomy catheter 22" to be moved longitudinally with respect to the guide catheter and the guide wire, a source 110 of compressed gas, e.g., nitrogen or air, to power the drive sub-system, a debris removal sub-system 30 made up of an extraction pump 90 and associated components, and a control console 204.

Figure 14:
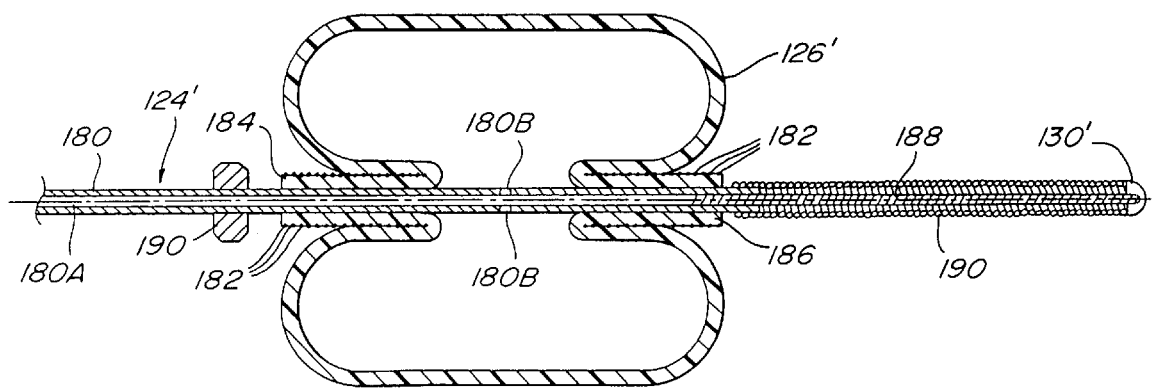
FIG. 14 is an enlarged longitudinal sectional view similar to FIG. 8, but showing a modified guide wire and distally located balloon for use with the systems of this invention.

The guide wire 124" is shown clearly in FIG. 14 and is similar to the guide wire 124 in that it includes an inflatable balloon 126" located immediately adjacent the distal end of the guide wire 124", a flexible distal end portion 128" immediately distally of the balloon 126" and terminating in an atraumatic tip 130" at the distal end of the guide-wire 124". However, the guide wire 124" is not arranged to perfuse downstream tissue, as is the case of the guide wire 124. Thus, as can be seen in Fin 14 the guide wire 124' basically comprises an elongated small diameter, flexible, hollow wire or tube 180, e.g., a "hypo" tube formed of type 304 stainless steel having a 0.010 inch outside diameter and a 0.005 inch inside diameter. A central passageway or bore 180A extends the full length of the guide-wire tube 180.

The balloon 126' is formed of any suitable material, e.g., latex of a thickness of approximately 0.006 inch, and is fixedly secured slightly proximally of the distal end portion of the tube 180 via a plurality of loops or lashes of a filament 182, e.g, polypropylene, wrapped about the tubular proximal end portion 184 of the balloon 126' and similar loops or lashes 182 wrapped about the tubular distal end portion 186 of the balloon 126'. This creates a confined space within the balloon and into which an inflation gas, e.g., carbon dioxide, is to be provided via the guide-wire tube 180 to inflate the balloon. To that end plural gas ports 180B extend through the wall of the guide-wire tube 180 in communication with the interior of the balloon and with the central passageway 180A in the guide-wire tube 180. The balloon can be any suitable size, depending upon the application. For example, for revascularizing a typical bypass graft, the outside diameter of the balloon when deflated may be approximately 0.03 inch, and may be inflated to an outside diameter of up to 0.2 inch (5 mm).

A tapered, flexible, core wire 188, e.g., type 304 stainless steel, is soldered by any suitable lead-free solder into the distal end of the central passageway 180A of the guide-wire tube 180 to seal its distal end. A tight helix or coil 128' is also soldered by a lead-free solder to the outer surface of the distal end of the tube 180. The coil 128' forms the curved, flexible distal end of the guide-wire and can be fabricated of any suitable radiopaque material, e.g., platinum wire of 0.003 inch diameter. The coil 190 extends for a short distance, e.g., approximately 1 inch, from the end of the tube 180 and is of a suitably small outside diameter, e.g, 0.018 inch. The distal end of the core 188 extends into a small bore in the atraumatic tip 130' and is soldered in place by a lead-free solder. The distal end of the coil 128' is also soldered to the atraumatic tip by a lead-free solder. The atraumatic tip 130' is in the form of a hemisphere of any suitable material, e.g., type 300 stainless steel.

A small sleeve or ring 190 formed of any suitable material, e.g., plastic or stainless steel, is located on the guide wire 124' immediately proximally of the balloon 126'. This ring serves as a stop member for the atherectomy catheter 22". In particular, as the atherectomy catheter 22" is advanced along the guide wire 124', with the guide wire 124' and the guide catheter 24 being held in a fixed position with respect to each other and to the patient's vascular system by a cradle assembly (to be described later), the rotating working head 32" will be prevented from engaging and perforating the distally located balloon by the ring or stop 190. Thus, the advancement of the working head along the guide wire to remove the plaque or other restriction-forming material in the vessel will not present any danger of perforating the balloon.

The console 204 is similar to console 102 described heretofore and includes various electrical and electronic components, e.g., a microprocessor and associated circuitry to accomplish the various functions of the system and to display various system parameters. Thus, as can be seen clearly in FIG. 9B, the console 204 includes the heretofore identified peristaltic infusion pump 84 and the peristaltic extraction pump 90. Compressed gas, e.g., nitrogen, is provided via line 112 from the tank 110. The tank provides the compressed nitrogen via heretofore identified regulator 74 and associated valve 76 into line 112 and from there to line 72. The gas pressure is displayed on a dial or meter 78 on the front of the console. Control of the turbine's rotational speed is effected by a turbine speed adjustment knob 206 on the front console. The turbine's speed is displayed on a digital display panel 208. An optical signal indicative of the turbine's speed is provided via a fiber optic line 210A. This line is connected to a connector 212A on the console. Another fiber optic line 210B is connected to another connector 212B on the console, whereupon a beam of light from the console is carried down line 212B to the turbine rotor where it is broken or chopped up by the rotating blades. The chopped up light beam which is indicative of rotor speed is carried back to the console via line 210A and connector 212A. Control of the turbine is effected via a turbine foot control (or hand control, not shown) 114 connected via line 116 to a connector 214 on the console.

A pressure transducer 218 (FIG. 9A) is connected in the line 86 coupled from the infusate pump 84 to the atherectomy catheter 22". The pressure transducer provides an output signal via a line 220 to a connector 222 (FIG. 9B) on the console. The rate of infusion liquid flow into the atherectomy catheter 22" is effected by the heretofore identified peristaltic pump 84. The speed of that pump is controlled via an up/down switch 224 on the console. The pump's speed in RPM is displayed on a digital readout panel 226. The speed of the extraction pump is controlled by an up/down switch 228 on the console and that pump's speed is displayed on an associated digital readout panel 230. The console also includes an on/off switch 232 for providing electrical power to the system when the switch is in the on position.

Data from the console, e.g., operating parameters, etc., is arranged to be downloaded to any suitable device, e.g., a laptop computer 216, via conventional multipin electrical connector 218, e.g., an RS 232 serial port, and associated cable 220.

If desired, the console 204 may also include various alarm devices to warn operating personnel of certain abnormal conditions. For example, the console may include a low battery power warning lamp on the front of the console to warn operating personnel that the battery is low. An infusate high pressure warning lamp may also be provided on the console along with an associated audible annunciator to produce respective visible and audible warning signals when a high pressure infusate condition exists.

Figure 12:
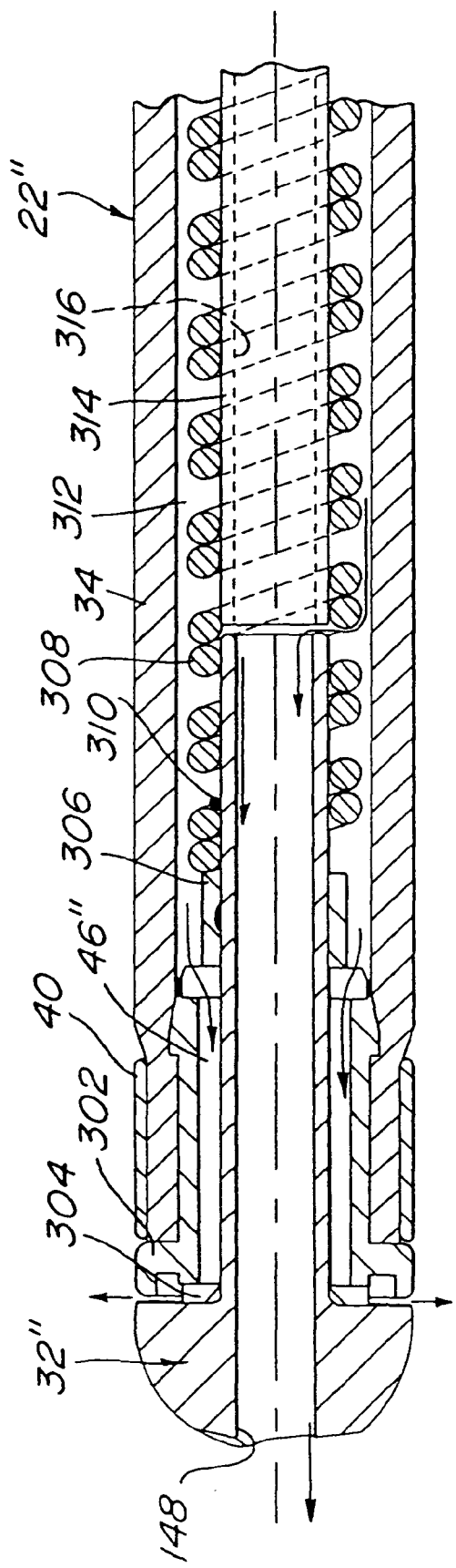
FIG. 12 is a greatly enlarged longitudinal sectional view of the distal end of an atherectomy catheter forming a part of the embodiment of the system of FIG. 9A.
Figure 13:
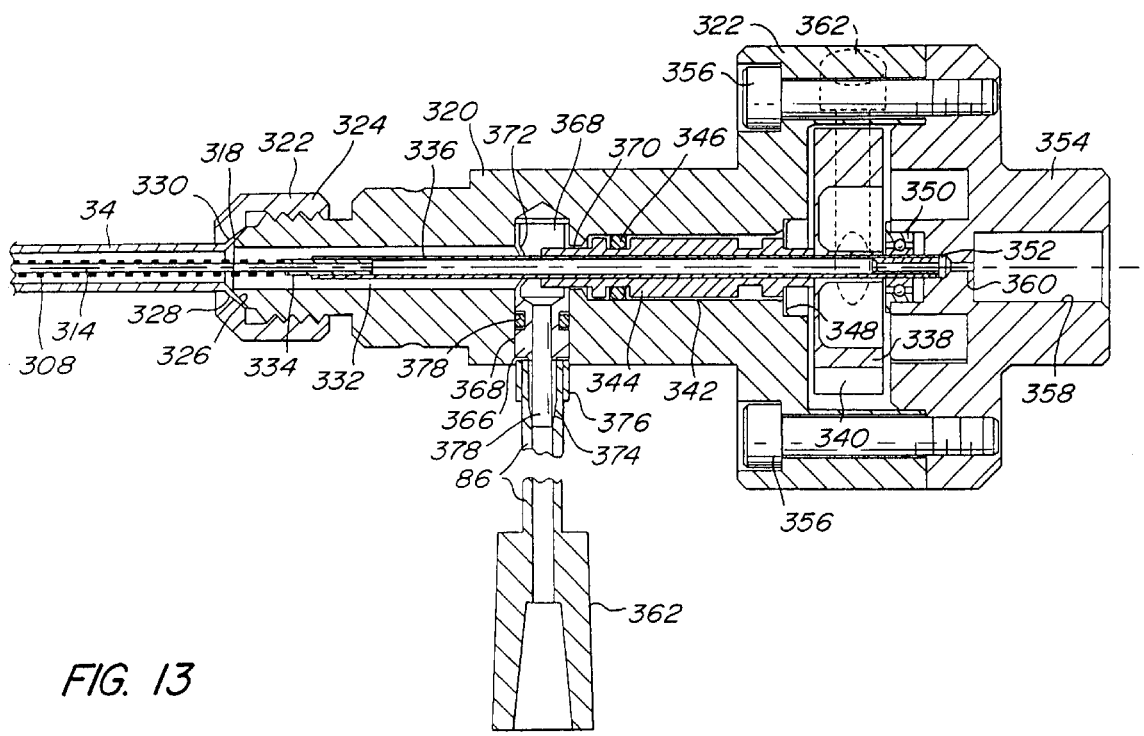
FIG. 13 is an enlarged longitudinal sectional view of the proximal end of the atherectomy catheter of the system of FIG. 9A.

Referring now to FIGS. 12 and 13, the details of the atherectomy catheter 22" will now be described. As can be seen that the catheter 22" is similar to catheter 22" in that it includes a jacket 34 having a distal end. A rotary working head or tip 32" is located at the distal end of the jacket. The tip 32 is preferably constructed in accordance with the teachings of U.S. Pat. No. 4,747,821. However, tip 32" unlike the tip of the aforementioned patent includes a central passageway or bore 148 through it (like tip 32'). It is through this bore that the guide wire 124 extends.

The working head 32" is mounted for rotation within a bushing 302 secured to the distal end of the jacket. The bushing 302 is similar in construction to the bushing of the U.S. Pat. No. 4,747,821 and it includes plural passages 46" extending along its length through which the infusate liquid passes to exit out of the tip. In addition it includes plural radial passageways 304 in the thrust pad portion forming the distal end of the bushing and which are in communication with the passages 46" through which the liquid exits radially. The radial passages are constructed similarly to those of U.S. Pat. No. 5,049,124 (Bayles) whose disclosure is incorporated by reference herein. Thus, the exiting liquid from those passages is impacted by the flattened sides of the tip to create a vortex flow in a manner similar to that as shown in FIG. 12. The rotary working head 32" also includes a tubular shank portion through which the central bore 148 extends. Infusate liquid from the passageway 312 is enabled to flow into the open proximal end of the bore 148 and through the annular space or clearance between the inner surface of that bore and the outer surface of the guide wire extending through the bore as shown by the arrows in FIG. 12. A sleeve 306 is located immediately proximally of the bushing 302 and extends about the shank portion of the rotary working head 32". The sleeve 306 is welded to the shank portion of the rotary working head. The rotary working head 32" is arranged to be rotated at a high rate of speed within the bushing by a drive cable 308. As best seen in FIG. 12, the cable 308 is a bifilar or double helix formed of any suitable material, e.g., 304 stainless steel or Nitinol, and is flexible so that the atherectomy catheter can be readily bent to follow tortuous paths to the revascularization site, i.e., the coronary bypass graft. The distal end helices of the drive cable 308 are welded at 310 to the shank portion of the rotary working head 32". The outer diameter of the drive cable is less than the inner diameter of the catheter jacket 34 to form an annular passageway 312 therebetween. This passageway extends the full length of the atherectomy catheter and serves to carry the infusion liquid to the working head 34".

A flexible plastic tube or sleeve 314 is located within the central passageway of the bifilar drive cable 308 and extends for the full length thereof. The tube 314 includes a central passageway 316 which is of approximately the same internal diameter as the bore 148 extending through the working head 32" and is coaxial therewith in order to accommodate the guide wire 124 therethrough. The sleeve 314 serves to form a barrier between the metal helices of the drive cable 308 and metal guide wire extending through it, while preventing the helices of the cable 308 from closing up as the drive cable is rotated.

In FIG. 13, there is shown the details of the proximal end of the atherectomy catheter 22". Thus, it can be seen that the proximal end of the jacket 34 is flared outward at 318. The flared proximal end of the jacket is connected to the distal end of a turbine housing or body 320 via a capture nut 322. The capture nut 322 includes internal threads 324 which mate with corresponding external threads on the distal end of the turbine housing 320. The free end of the turbine housing is tapered at 326. The capture nut 322 also includes a tapered inner surface 328 merging into a central bore 330 through which the catheter jacket 34 extends. Thus, when the nut 322 is tightened, the flared end 318 of the jacket is tightly interposed between the surface 330 of the nut and the tapered surface 326 of the turbine housing 320. The distal end portion of the turbine housing 320 also includes a central bore 332 into which the infusate fluid will be injected for flow into the annular passageway 312 in the atherectomy catheter, as will be described later.

The proximal end of the bifilar drive cable 308 is connected, e.g., welded, to an adaptor sleeve 334. The adaptor is a tubular member which is in turn welded to the turbine rotor drive shaft 336. The turbine drive shaft 336 is an elongated tubular member. Being tubular the turbine drive shaft 336 includes a central passageway. It is through this central passageway that the guide wire is arranged to be extended. The turbine rotor drive shaft 336 extends through the central bore 332 in the turbine housing and terminates at its proximal end in a seven-bladed turbine rotor 338. The rotor is located in an enlarged proximally located flanged portion 322 of the turbine housing 320. In particular, the flanged portion 322 includes a hollow interior chamber 340 in which the turbine blade 338 is located. An enlarged central bore 342 extends distally of the chamber 340 and is axially aligned with the central bore 332 in the distal portion of the turbine housing 320. A sleeve bearing 344 is located within the central bore 342. The turbine rotor shaft 336 extends through a central bore in the bearing with a slight clearance or leakage passageway, e.g., 0.0005 inch to form a fluid leakage path to facilitate the cooling of the bearing. An O-ring 346 is located within an annular recess in the distal portion of the sleeve bearing 344 to form a fluid-tight seal. A star washer 348 is located within an enlarged portion of the bore 342 to hold the sleeve bearing in place.

The proximal end of the turbine drive shaft 336 extends into a ball bearing assembly 350 to center the turbine shaft on the longitudinal axis of the housing. A guide-wire centerer and leakage control restrictor member 352 is located within the hollow proximal end of the turbine drive shaft 336. The guide wire 124 is arranged to pass through the restrictor where it is centered and then through the turbine drive shaft, the adaptor 334, the sleeve 314, and out through bore 148 in the working head 32". Moreover, air can pass through the interface of the restrictor 352 to cool and lubricate the adjacent surfaces. The ball bearing assembly 350 is held in place via a cap or cover 354. The cap 354 serves to close off the hollow interior of the turbine housing. To that end, the cap is releasably secured to the flanged proximal portion 322 of the turbine housing 320 via plural threaded bolts 356. An enlarged bore hole 358 is located within the cap 354 and is coaxially aligned with the central longitudinal axis of the drive shaft 336. A smaller diameter bore 360 communicates with the bore 358 and with the restrictor 352.

The compressed gas, e.g., nitrogen, to effect the rotation of the turbine is provided from the tank 110 via an inlet port 362. The pressurized gas enters the turbine housing portion 322 somewhat tangentially and impinges on the angled rotor blades 338 to cause the turbine rotor to rotate about its longitudinal axis at a high rate of speed. This effects the concomitant rotation of the drive shaft 336, the bifilar cable 308 and hence the rotary working head 32".

The infusate fluid, e.g., saline and a contrast medium (plus anything else which is desired to be introduced into the vascular system, such as heparin, growth factors, microspheres carrying chemicals, pharmaceuticals or other biologically active materials, etc.) is introduced into the turbine housing 320 so that it gains ingress into the passageway 332. From that passageway, it flows through the communicating passageway 312 extending within the jacket of the catheter to exit at the distal end of the jacket where the working head 32" is located. The means for introducing infusate liquid into the turbine housing comprises the tubing 86 on which a connector 362 is mounted. The connector 362 is arranged to be connected to the output of the infusate pump.

An interlock member 366 is located in a transverse bore 368 in the turbine housing 320 so that it perpendicularly intersects the longitudinally extending bore 332. The interlock member is a generally plug-like, tubular body having a thin walled upper end 368 defining an enlarged hollow interior space. An opening 370 is provided in the thin walled upper end of the interlock member communicating with the enlarged hollow interior space and into which the distal portion of the sleeve bearing 344 extends. Another opening 372 is provided diametrically opposed from the opening 370 so that the turbine drive shaft 336 can extend through the interlock member via the openings 370 and 372. The lower end of the interlock member 366 includes a barb-like tubular projection 374 which extends into the interior of the plastic tube 86. A ring-like ferrule 376 extends about the outer surface of the tube at the upper end thereof to capture the tube on the barb. A sealing O-ring 378 is disposed with in an annular recess extending about the periphery of the interlock member 366. The barb portion of the interlock member 366 includes a passageway 378 extending through it in communication with the hollow interior at the upper end of the interlock member. Thus, the infusion liquid introduced into the tube 86 will pass through the communicating passageway 378 in the barb member into the hollow upper interior 368 of the interlock member and out through opening 372 into the passageway or bore 332. From passageway 332, the infusater liquid will flow through the hollow annular passageway 312 in the catheter's jacket 34 and out through its distal end at the working head 32".

As will be appreciated by those skilled in the art, the rotation of the drive cable 308 creates an Archimedes-like pumping action to aid the infusate pump in carrying the infusate liquid down the annular passageway 312 in the jacket 34. In particular the ability of the helical drive cable 308 to deliver flow is a function of: (1) the rotation speed of the helix, (2) the swept volume of the helix (the swept volume of the helix being the volume of fluid entrapped between the coils of one pitch of the helix), and (3) the leakage of flow back along the helix due to the clearance between the helix and the jacket and the clearance between the helix and the liner. If the clearances are reduced to zero (leakage reduced to zero) the pump can act as a very stiff positive displacement pump, that is, it can deliver flow at a large range of output pressures regardless of the inlet pressure. For example, with a 5 F diameter catheter having bifilar drive cable with 0.008 inch wire diameter and pitch of 0.040 inch running at speeds between 100,000 and 160,000 RPM, the helix design suitable for transmitting suitable torque, with adequate flexibility for navigating the bends of the coronary vasculature, also has the correct swept volume to deliver an appropriate flow, e.g., 30-40 mL/minute, required to keep the catheter and tip abrasion site at a temperature compatible with tissue viability (e.g., not more than 98 deg F.). These facts make it possible for a 5F catheter system to use the helical drive cable 308 as the infusate metering pump while the peristaltic infusate pump 84 serves as a priming pump. This arrangement, can deliver pressure rather than flow by the use of soft pump tubing, i.e., tubing that leaks back under the pump 84 rollers, if the delivery pressure becomes excessive, e.g., approximately 30 psi or greater. If different size catheters are used, such as 8 F or 4 F, the helical drive cable design may not provide the ideal flow, and the peristaltic infusate pump 84 characteristics might well have to be changed to obtain the correct flow. This can be accomplished by changing the peristaltic pump speeds, changing the stiffness of the peristaltic pumps by using tubing of different softness, and partially disabling the helix drive cable pump by increasing the clearances around the helix. Thus, if the console provides for independently adjustable peristaltic pump speeds for the infusate and extraction pumps, the system can provide for any catheter design. The operator can be instructed to select the appropriate pump speed and the appropriate pump tubing for whatever catheter is in use. In some instances it may be advisable to use operator adjustable peristaltic pumps linked electronically that provide for fixed ratios between the infusate and extraction pumps, and in other designs it may be best to provide for the pumps to be preset and not user adjustable.

It has also been found that there is an advantage to having a variable pitch helix for the drive cable 308. Thus, the cable 308 is preferably so constructed. As will be appreciated if the drive cable 308 is to act as a pump in addition to the means for effecting the rotation of the working head, the helices of the cable have to have a certain pitch (e.g., 25 coils to the inch) to provide the required swept volume. If the bending stiffness of the atherectomy catheter is to be minimized (e.g., to enable the catheter to freely negotiate tortuous paths to the site of the occluded vessel section) the helices of the cable needs to be approximately of closed coil configuration (e.g., 40 coils to the inch), but not quite closed, because it is best if the coils do not touch each other as the catheter bends since the friction between the abutting coils may cause excessive heat to be generated. It has been found that if the distal end portion of the helical drive cable 308 is almost close wound for a short distance (e.g., 0.5 to 4.0 inches), as is the case in the embodiment shown herein, the remainder of the cable, (i.e., the portion located proximally of the distal end portion and which may be approximately 50 inches or longer) can force the infusate liquid past the close coils at the distal end and out of the catheter. The variable pitch of the drive cable thus provides for the optimum pumping action, while maintaining optimum flexibility. As will also be appreciated the helix pitch of the drive cable also has an affect on vibration of the catheter, with the coarser or greater spacing between helicies resulting in lower vibration. Thus, the variable pitch drive cable 308 will also help to reduce the vibration level by minimizing the length of closed coil helices at the distal end of the drive cable.

As mentioned earlier, the system 200 includes a cradle assembly 202 for holding the guide catheter 24 and the guide wire 124 fixed with respect to each other and with respect to the patient's vascular system, while supporting a portion of the atherectomy catheter to enable it to be moved longitudinally with respect to the guide catheter and guide wire in order to advance the working head through the vessel section to be revascularized. The cradle assembly 202 will now be described with reference to FIG. 9A. As can be seen therein, the cradle assembly basically comprises a cradle member 400 (shown by phantom lines in the interest of drawing simplicity) and other associated components (some shown by solid lines and others by phantom lines), all to be described later. The cradle member 400 itself is a generally tubular member which is arranged to support the turbine body therein and to allow the turbine body to slide longitudinally with respect to the cradle member 400 while fixing the position of the guide catheter 24 and guide wire 124 relative to each other.

The tubular cradle 400 includes a loading slot 402 extending from its front or distal end to a point close to its rear or proximal end. A pair of support feet 404, also shown by phantom lines, are provided on the underside of the cradle tube to support it on any horizontal surface. A cup-shaped plug member 406 is mounted in the open rear end of the cradle tube. The plug member includes a central passageway 408 extending through it. A pair of telescoping tubes 410 and 412, are mounted between the central passageway in the plug member and the proximally located cap 354 of the turbine housing 320 via a ferrule (not shown). The central passageway 408 in the plug member and the associated telescoping tubes 410 and 412 provide a passageway through which the guide wire 124 may be extended into the turbine housing and from there through the atherectomy catheter 22" as described earlier. The telescoping tubes are formed of any stiff material, e.g., type 304 stainless steel, to prevent buckling of the guide wire.

In order to fix or clamp the longitudinal position of the guide wire with respect to the cradle assembly while also forming a fluid tight seal about the guide wire where it enters the plug member 406, a conventional hemostasis valve, e.g., a Tuohy Boist valve 412, is mounted on the rear side of the plug member via a wing nut mount (not shown).

The turbine housing assembly is mounted within the cradle tube for sliding movement therealong in order to adjust the distance that the working head 34" extends from the distal end of the guide tube 24. This feature enables the rotary working head to be advanced in the distal direction to open a lumen through the plaque or other material forming the restriction in the bypass graft to be revascularized. To achieve that end, a handle 416 is provided for the turbine housing and projects radially outward from the turbine housing portion 322. The handle extends through a longitudinally extending linear slot 418 in the cradle tube 400. It should be pointed out at this juncture that the handle and the associated slot are shown on the facing side of the turbine tube (i.e., the visible side in FIG. 9), when in reality they are located on the opposite side. The showing of the handle and slot on the facing side of the cradle tube is merely done for drawing convenience.

In order to increase the "wheel base" of turbine housing so that it slides easily within the cradle tube 400 in a longitudinal direction without tilting or canting, a turbine tube housing extension member 420 is mounted, i.e., snap-fit, on the distal portion of the turbine housing. The extension member 420 includes a central opening through which the atherectomy catheter 22" exits the turbine housing.

A manifold member 422 is mounted within an extension adjustment tube 424 at the front end of the cradle tube 400. The extension adjustment tube is a slotted tube which telescopes within the front end of the cradle tube 400 and whose position can be adjusted so that the manifold 422 can be moved closer or further away from the cradle tube. This feature enables the system 200 to be used with guide catheters of varying lengths. In order to fix the position of the extension adjustment tube with respect to the cradle tube 400, a tube extension latch 426 is provided to extend through any selected one of plural longitudinally spaced holes 428 in the extension tube and a single aligned hole not shown in the front end of the cradle tube.

The manifold 422 is a disk-like member having a longitudinal passageway (not shown) extending therethrough and to which the proximal end of the guide catheter 24 is connected via a swivel connector 430. The swivel connector permits one to adjust the angular orientation of the guide catheter with respect to the cradle tube so that the guide catheter can be revolved to any rotary position necessary to obtain compatibility with the patient's vascular anatomy. The longitudinal passageway of the manifold is in fluid communication with the proximal end of the annular passageway 312 extending down the interior of the atherectomy catheter's jacket. The manifold also includes a radially extending side port (not shown) in communication with the longitudinal passageway at the proximal end of the guide catheter. The extraction (vacuum) tube 88 is arranged to be connected to the radial side port of the manifold via conventional connector 432 to withdraw blood, infusate liquid and debris which has been drawn down the passageway between the guide catheter and the atherectomy catheter by the action of the extraction pump 90.

Since the atherectomy catheter 22" extends through the guide catheter 24, a conventional hemostasis valve 434 is mounted on the rear (proximal) side of the manifold 422 to enable to the atherectomy catheter to extend through the longitudinal passageway in the manifold and into and through the guide catheter 24.

A stiffener tube 436 is provided on the atherectomy catheter between the turbine housing and the manifold to prevent the atherectomy catheter's jacket 34 from buckling under axial loads. The stiffener tube also facilitates the assembly and loading of the atherectomy catheter into the cradle tube. To that end, a hook wire 438 is mounted on the stiffener tube 436 to facilitate movement of the stiffener tube. A pair of pivotable trunnions 440 project outward from the distal end portion of the stiffener tube for connection to diametrically opposed portions of the extension tube 424 to center the stiffener tube so that it can be lifted to enable loading of the atherectomy catheter.

In accordance with one preferred embodiment of the invention, the longitudinally extending slot 402 is of sufficient length to enable the turbine housing and hence the atherectomy catheter 22" to be reciprocated through a 4-5 inch range.

It must be pointed out again that the subject invention is not limited to atherectomy catheters, and particularly rotary head catheters. In particular, the subject invention may incorporate an instrument having any other type of working head, e.g., a balloon angioplasty catheter, a catheter for injecting a restriction-removing or dissolving liquid, an ultrasonic catheter, a laser catheter, a stent-delivery catheter, etc., for opening a lumen in an occluded vessel. To that end the term "working head" as used herein is meant to include any type of device for operating on an occluded vessel to open a lumen in that vessel to the freer flow of blood therethrough.

Figure 16:
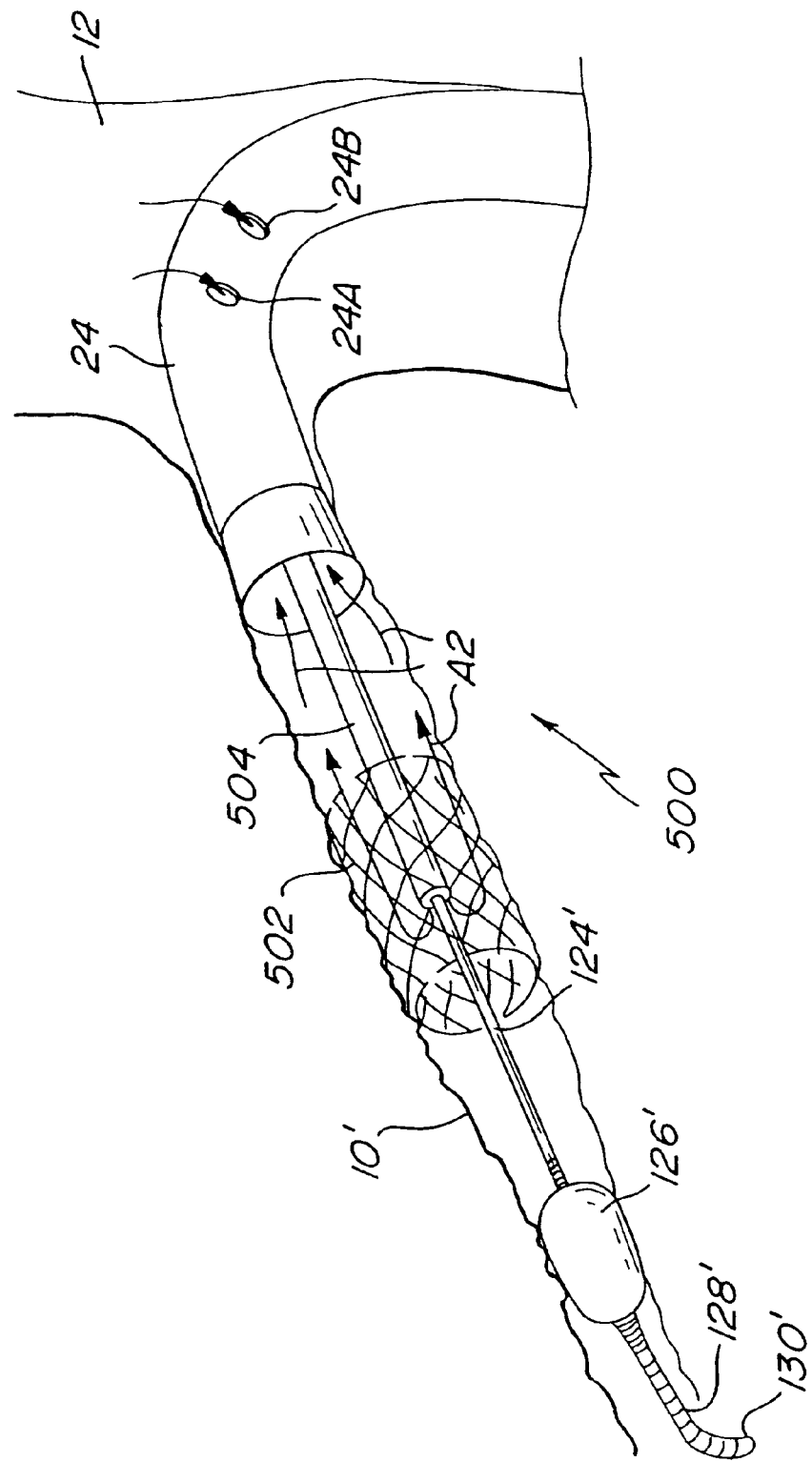
FIG. 16 is a view similar to that of FIG. 10 but showing a method of providing a stent in an occluded blood vessel section, e.g., a bypass graft, to revascularize it, and with the debris extraction system making use of a guide catheter tightly engaging the wall of the blood vessel section.

In FIGS. 16 and 17 there are shown yet another alternative embodiment of a revascularization system 500 of this invention. The system 500 is arranged to revascularize an occluded blood vessel, e.g., a bypass graft 10', by introducing a conventional expandable stent 502 into a lumen formed in the restrictive material of the occluded blood vessel section, e.g., the bypass graft. If desired, the system 500 may also employ the atherectomy catheter and some associated components of the system 200 described heretofore to effect the opening of a lumen through the material forming the restriction, followed by the introduction of a stent-delivery catheter (not shown) for carrying the stent 502 in a collapsed state into the lumen created by the atherectomy catheter, and then to expand the stent 502 in that lumen to the state shown in FIGS. 16 and 17 to ensure that the lumen stays open. The stent-delivery catheter used in such an application may be of any conventional type, e.g., a balloon catheter.

It must be pointed out at this juncture that the system 500 may be used without an atherectomy catheter, like the catheters described above or any prior art restriction-opening device, for initially forming the lumen through the material forming the restriction. In such an alternative application, as will be described later, the system 500 makes use of any suitable conventional stent-delivery catheter to carry the collapsed stent 502 over a guide wire, like guide-wire 124' or any other suitable balloon bearing guide-wire, through the restriction in the occluded blood vessel to an operative position, whereupon the stent-delivery catheter is operated, e.g., its balloon inflated, to expand and place the stent in position (like shown in FIGS. 16 and 17).

Irrespective of the manner in which the lumen is created into which the stent 502 is placed, the system 500 of this invention makes use of a debris removal sub-system to remove any particles or other debris produced during the revascularization/stenting procedure. That debris removal system may be similar to that described earlier, or any other suitable type. As shown in the embodiments of FIGS. 16 and 17, the debris removal sub-system used to remove any particles or debris produced during the revascularization/stenting procedure basically comprises a guide catheter 24 having at least one control port, like that described above, and another catheter 504 (to be described later) for delivery of an infusate or irrigation liquid from some pumping means, e.g., an infusate pump 84, into the occluded vessel section, and some pumping means, e.g., an extraction pump 90, coupled to the interior of the guide catheter 24 to effect the removal of blood, the infusion liquid and any debris created during the restriction opening procedure from the patient. It should be noted that the "other catheter 504" for delivery of the infusate or irrigation liquid to the situs of the vessel portion being revascularized, may comprise an atherectomy catheter 22" like that described with respect to system 200 when such a system is used to form the lumen into which the stent will be placed, or may comprise a separate catheter, tube, or conduit, or may comprise a lumen or passageway in the guide catheter 24 separate and apart from the central passageway through which the debris, blood and infusate liquid is removed. In the embodiment shown the catheter 504 for carrying the infusion or irrigation liquid into the situs where the stent is to be placed basically comprises a simple irrigation tube or catheter formed of a flexible material, e.g., a plastic, and having a central passageway or lumen extending fully therethrough for carrying the infusate or irrigation liquid from a pump, like pump 84 or any other suitable source of irrigation liquid, down the lumen and out of its open end to the operative situs like shown in FIGS. 16 and 17.

If it is desired to utilize a system 500 to apply the stent 502 into a lumen formed by an atherectomy catheter, e.g., atherectomy catheter 22", the procedure to be followed basically comprises the following steps. First the guide catheter 24 is placed in position so that its distal end is located proximally of the restriction to be opened and its control or regulation port(s) 24A/B is(are) in fluid communication with an upstream patent vessel, e.g., the aorta, like shown in FIGS. 10, 11, 16 and 17. The guide wire 124" is then extended through the guide catheter 24 and through the restriction to be opened so that the distally located balloon (obturator) 126 on the guide wire is downstream of the restriction. The balloon 126 is then inflated to block the vessel to be revascularized downstream of its restriction. The extraction pump 90 is then operated to evacuate any debris particles which may have been produced by the passage of the guide wire 124 and balloon 126 through the restriction and by the inflation of the balloon 126. The atherectomy catheter 22" is then passed over the guide wire through the guide catheter so that its working head 32" extends out of the open end of the guide catheter and is at the situs of the restriction to be opened.

The atherectomy catheter 22" (or any other catheter having a restriction opening working head) is then operated in a manner like described above to enable the working head to open a lumen through the restriction, while the debris removal sub-system removes the debris created by that operation along with blood and the infusate liquid through the guide catheter. The control or regulation ports in the guide catheter ensure that the vessel being revascularized does not collapse during the procedure.

Once the lumen has been created through the restriction, the atherectomy catheter can be removed, while maintaining the vacuum, i.e., keeping the extraction pump 90 operating. After removal of the atherectomy catheter the extraction pump 90 can be stopped. If it is desired to give the patient some recovery time before deployment of the stent 502, the distal balloon on the guide wire may be deflated, thereby enabling blood to flow through the newly formed lumen in the revascularized vessel to the downstream vessel, e.g., a coronary artery 15. Once sufficient time for the patient to recover has elapsed (assuming that any recovery time is desired) the distally located balloon 126 is then re-inflated.

The stent-delivery catheter (not shown) is then introduced through the guide catheter and over the guide wire until its working head, e.g., the balloon on which the collapsed stent 502 is located, is within the lumen created by the atherectomy catheter 22". The stent-delivery catheter is then operated, e.g., its balloon inflated, to expand the stent 502 radially outward and into seating engagement with the revascularized vessel section, like that shown in FIGS. 16 and 17. If desired, the debris removal system may be operated to withdraw any debris particles created by the deployment of the stent. Once the stent has been deployed the stent-delivery catheter can be removed, e.g., its balloon deflated and then the catheter withdrawn proximally along the guide wire. The guide catheter can then be removed.

In some applications it may be desirable to provide an irrigation or infusate liquid into the lumen in which the stent is to be deployed during or immediately after the stent deployment the procedure. To that end, an irrigation tube 504 (like that shown in FIGS. 16 and 17) may be introduced over and along the guide wire 124' and through the guide catheter 24 so that its open distal end is in communication with the situs of the stent while the distally located balloon (obturator) 126' remains inflated. An irrigant liquid can then be introduced via the irrigation tube to flush out any debris via the passageway between it and the guide catheter under the action of the extraction pump 90 or any other suitable pump or vacuum source. Once this has been accomplished the irrigation tube 504 can then be withdrawn over the guide wire, while the vacuum is maintained, e.g., the pump 90 operates, to remove any debris which may be produced by the removal of the irrigation tube. The vacuum (e.g., pump 90) can then be stopped, the balloon 126' on the distal end of the guide-wire 124' can then be deflated and the guide wire can then be withdrawn through the guide catheter 24. Then the guide catheter can be removed.

If it is desired to place a stent 502 within an occluded blood vessel section, without having first opened a lumen through it with an atherectomy catheter, like catheter 22" or any other lumen-opening catheter, the procedure to be followed using the system 500 basically comprises the following steps. First the guide catheter 24 is placed in position so that its distal end is located proximally of the restriction to be opened and its control or regulation port(s) 24A/B is(are) in fluid communication with an upstream patent vessel, e.g., the aorta, like shown in FIGS. 10, 11, 16 and 17. The guide wire 124' is then extended through the guide catheter 24 and through the restriction to be opened so that the distally located balloon (obturator) 126' on the guide wire is downstream of the restriction. The balloon 126' is then inflated to block the vessel to be revascularized downstream of its restriction. The stent-delivery catheter (not shown) is then introduced through the guide catheter 24 and over the guide-wire 124' until its working head, e.g., the balloon on which the collapsed stent 502 is located is at the desired position within the vessel to be revascularized. The debris removal sub-system, or any other extraction or vacuum system, is then operated to withdraw any debris or particles created when the stent is deployed. Thus, once the debris removal sub-system is operating the stent-delivery catheter can then be operated, e.g., its balloon inflated, to expand the stent 502 radially outward thereby enlarging the lumen through the restriction seating the stent in place against accidental dislodgement within the blood vessel section, like that shown in FIGS. 16 and 17. Once the stent has been deployed the stent-delivery catheter can be removed, e.g., its balloon deflated, and then the catheter withdrawn, e.g., slid proximally along the guide-wire 124' until it is out of the being's body. An irrigation or infusate liquid is then provided into the operative situs, i.e., the situs of the stent, to flush away any debris created during the stent deployment procedure. To that end, an irrigation tube 504 is introduced along the guide wire 124' and through the guide catheter 24 so that its open distal end is in communication with the situs of the stent, while the distally located balloon (obturator) 126 remains inflated. An irrigant liquid can then be introduced via the irrigation tube 504 to flush out any debris via the passageway between it and the guide catheter 24 under the action of the extraction pump 90 or any other suitable pump or vacuum source.

Once the stent is deployed and all debris removed, the irrigation tube can then be withdrawn from the being by sliding it out over the guide-wire 124', while the vacuum is maintained, e.g., the pump 90 operates, to remove any debris which may be produced by the removal of the irrigation tube. As described earlier, the control or regulation port(s) 24A/B ensure that the vessel section being revascularized does not collapse during the revascularization procedure.

After removal of all remaining debris, the vacuum (e.g., pump 90) can then be stopped, the balloon 126 on the distal end of the guide-wire can then be deflated and the guide wire can then be withdrawn through the guide catheter. Then the guide catheter can be removed.

Irrespective of the type of revascularization procedure utilized, it maybe desirable before removal of the guide catheter 24 to inject a dye through it to the operative situs to enable one to fluoroscope or otherwise visualize the bypass vessel to ensure that it has been be properly revascularized.

Without further elaboration the foregoing will so fully illustrate our invention that others may, by applying current or future knowledge, adopt the same for use under various conditions of service.

What is claimed is:

1. An lumen opening device for treating a lumen in a blood vessel portion of a living being's vascular system, said device comprising an outer catheter, an instrument having an inner catheter, a working head, and pump means, said instrument arranged to be extended through said outer catheter to form a passageway therebetween, wherein said pump means comprises at least one helical pump with said working head of said instrument being arranged to operate on occlusive material in a blood vessel's interior portion to open a lumen therein for the freer flow of blood therethrough, whereupon some debris may be produced by the operation of said working head, said catheter comprising a distal end portion and being arranged such that the tolerances between said catheter and said helical pump allow said catheter to be flexible, said pump means introducing an infusate liquid at a first flow rate at said working head and withdrawing said liquid at a second and higher flow rate to create a differential flow in said lumen, whereupon at least a portion of any debris produced by the operation of said working head is withdrawn by said at least one helical pump through said passageway for collection remote from the occluded vessel portion and is prevented front flowing into any upstream blood vessel or downstream blood vessel.

2. The intravascular device of claim 1 wherein said at least one helical pump also serves as a helical drive cable.

3. The intravascular device of claim 2 wherein said helical drive cable comprises a two start helical spring.

4. The intravascular device of claim 2 wherein said helical drive cable is arranged with variable pitch.

5. The intravascular device of claim 1 wherein said catheter comprises an introducer sheath or guide catheter.

6. The intravascular device of claim 1 wherein said infusate comprises therapy means.

7. The intravascular device of claim 6 wherein said therapy means comprises a drug, pharmaceutical, a biologically active material, or microspheres carrying chemicals.

8. The intravascular device of claim 7 wherein said biologically active material comprises a growth factor.

9. The intravascular device of claim 7 wherein said drug comprises heparin or urokinase.

10. The intravascular device of claim 1 additionally comprising a debris blocking member.

11. The intravascular device of claim 10 wherein said debris blocking member comprises a balloon.

12. The intravascular device of claim 1 wherein said infusate liquid is introduced adjacent said working head.

13. The intravascular device of claim 1 wherein said infusate liquid exits said working bead.

14. The intravascular device of claim 13 wherein said working head is rotatable.

15. The intravascular device of claim 13 wherein said working head is arranged to introduce said infusate liquid in the form of liquid jets.

16. The intravascular device of claim 13 wherein said helical pump also serves as a helical drive cable.

17. The intravascular device of claim 15 wherein said working head does not engage occlusive material.

18. The intravascular device of claim 1 wherein said working head is arranged to introduce said infusate liquid in the form of liquid jets.

19. The intravascular device of claim 1 wherein said working head comprises an occlusion opening device.

20. The intravascular device of claim 2 wherein said working head comprises an occlusion opening device.

21. The intravascular device of claim, 19 wherein said device comprises a balloon angioplasty catheter, an ultrasonic catheter, a laser catheter, a stent-delivery catheter, a rotary abrasive head, or a rotary cutting head.

22. The intravascular device of claim 20 wherein said device comprises a balloon angioplasty catheter, an ultrasonic catheter, a laser catheter, a stent-delivery catheter, a rotary abrasive head, or a rotary cutting head.

23. The intravascular device of claim 22 wherein said rotary cutting head comprises an impeller.

24. The intravascular device of claim, 20 wherein said working head comprises a balloon angioplasty catheter, an ultrasonic catheter, a laser catheter, a stent-delivery catheter, a rotary abrasive head, or a rotary cutting head.

25. The intravascular device of claim 23 wherein said impeller is arranged to be rotated by said helical drive cable.

26. The intravascular device of claim 25 wherein said instrument further comprises a distal end with a shroud attached thereon.

27. The intravascular device of claim 26 wherein said shroud is arranged to cover said working head, and said shroud comprises an opening.

28. The intravascular device of claim 27 wherein said impeller projects out of said opening.

29. The intravascular device of claim 27 wherein any debris produced is progressively reduced in size until it is aspirated.

30. The intravascular device of claim 29 wherein said infusate expedites the treatment.

31. An intravascular system for treating a lumen in a portion of blood vessel of a living being's vascular system, said blood vessel being occluded by an occlusive material, said intravascular system comprising a lumen-opening member for introduction into the lumen of the blood vessel, debris blocking means, and pump means, said lumen-opening member being arranged to act on the occlusive material in the interior of the occluded blood vessel to open the lumen for the freer flow of blood therethrough, said lumen opening member comprising a working head, whereupon some debris may be produced from the occlusive material by the action of said lumen-opening member, said debris blocking means being arranged to be located within the occluded blood vessel distally of said lumen opening member for preventing debris from flowing distally of said debris blocking means, said pump means introducing an infusate liquid at a first flow rate and withdrawing said liquid at a second and higher flow rate to create a differential flaw adjacent said lumen-opening member, said infusate liquid comprising therapy means, whereupon arty debris produced by the action of said lumen-opening member is withdrawn with said liquid by said differential flow for collection remote from the occluded vessel portion and is prevented from flowing into any upstream blood vessel or downstream blood vessel.

32. The intravascular system of claim 31 wherein said intravascular system comprises a catheter, said infusate liquid and the debris therein being withdrawn from the occluded blood vessel portion through said catheter.

33. The intravascular system, of claim 31 wherein said therapy comprises a drug, pharmaceutical, a biologically active material, or microspheres carrying chemicals.

34. The intravascular system of claim 33 wherein said biologically active material comprises a growth factor.

35. The intravascular system of claim 33 wherein said drug comprises heparin or urokinase.

36. The intravascular system of claim 31 wherein said infusate liquid is introduced adjacent said working head.

37. The intravascular system of claim 31 wherein said infusate liquid exits said working head.

38. The intravascular system of claim 32 wherein said infusate liquid exits said working head.

39. The intravascular system of claim 38 wherein said working head is arranged to introduce said infusate liquid in the form of liquid jets.

40. The intravascular system of claim 39 wherein said working head does not engage occlusive material.

41. The intravascular system of claim 40, wherein said working head further comprises a thrombectomy device.

42. The intravascular system of claim 41. wherein said therapy comprises urokinase.

43. The intravascular system of claim 31 wherein said working head is arranged to introduce said infusate liquid in the form of liquid jets.

44. The intravascular system of claim 31 wherein said working head comprises any occlusion opening device, 45. The intravascular system of claim 44 wherein said device comprises a balloon angioplasty catheter, an ultrasonic catheter, a laser catheter, a stent-delivery catheter, a thrombectomy device, a rotary abrasive head, or a rotary cutting head.

46. The intravascular system of claim 31 wherein said working head comprises an ultrasonic catheter.

47. The intravascular system of claim 31 wherein said intravascular system additionally comprises a second catheter.

48. The intravascular system of claim 47 wherein said second catheter is arranged to deliver said infusate or irrigation liquid.

49. An intravascular system for treating a lumen in a blood vessel of a living being, the blood vessel being occluded by an occlusive material therein, said intravascular system comprising a working head, a pump moans, and barrier means, said working head being arranged to operate on the occlusive material in the interior of the occluded blood vessel to open a lumen therein for the freer flow of fluid therethrough, whereupon some debris may be produced from the occlusive material by the operation of said working bead, said barrier means being arranged for location downstream of said working head and activatable to restrict the flow of the debris downstream of said barrier means, said pump means introducing an infusate liquid at a first flow rate at said working head and withdrawing said liquid at a second flow rate higher than said first flow rate, thereby creating a differential flow, said infusate liquid comprising therapy means, whereupon any debris produced by the operation of said working head is withdrawn with said liquid by said pump means for collection remote from the occluded vessel portion.

50. The intravascular system of claim 49 wherein said barrier means comprises an expandable member.

51. The intravascular system of claim 50 wherein said expandable member comprises a balloon.

52. The intravascular system of claim 49 wherein said therapy comprises a drug, pharmaceutical, a biologically active material, or microspheres carrying chemicals.

53. The intravascular system of claim 52 wherein said biologically active material comprises a growth factor.

54. The intravascular system of claim 52 wherein said drug comprises heparin or urokinase.

55. The intravascular system of claim 49 wherein said system additionally comprises a flexible instrument and wherein said working head comprises a portion of said instrument, said instrument being arranged to be passed through the being's body so that said working head is located adjacent the occluded vessel portion.

56. The intravascular system of claim 55 wherein said barrier means forms a portion of a guide wire, said guide wire extending through said instrument.

57. The intravascular system of claim 56 wherein said guide wire is arranged to provide a perfusion liquid downstream of said barrier means.

58. The intravascular system of claim 56 wherein said barrier means comprises an expandable member.

59. The intravascular system of claim 57 wherein said perfusion liquid comprises said infusate, blood, or oxygenated liquid.

60. The intravascular system of claim 59 wherein said infusate is oxygenated.

61. The intravascular system of claim 57 wherein said perfusion liquid comprises said infusate liquid and said therapy comprises a drug, pharmaceutical, or a biologically active material.

62. The intravascular system of claim 61 wherein said biologically active material comprises a growth factor.

63. The intravascular system of claim 61 wherein said drug comprises heparin or urokinase.

64. The intravascular system of claim 58 wherein said expandable member comprises a balloon.

65. The intravascular system of claim 49 wherein said infusate liquid is introduced adjacent said working head.

66. The intravascular system or claim 49 wherein said infusate liquid exits said working head.

67. The intravascular system of claim 66 wherein said working head is arranged to introduce said infusate liquid in the form of liquid jets.

68. The intravascular system of claim 67 wherein said working head does not engage occlusive material.

69. The intravascular system of claim 68 wherein said working head further comprises a thrombectomy device.

70. The intravascular system of claim 49 wherein said therapy comprises urokinase.

71. The intravascular system of claim 49 wherein said working head comprises a balloon angioplasty catheter, an ultrasonic catheter, a laser catheter, a stent- delivery catheter, a thrombectomy device, a rotary abrasive head, or a rotary cutting, head.

72. The intravascular system of claim 55 wherein said working head comprises an ultrasonic catheter.

73. A method for treating a lumen in a portion of a blood vessel of a living being's vascular system, the blood vessel portion being occluded by an occlusive material, the occluded blood vessel portion being located distally of a patent blood vessel portion, said method comprising:
(a) extending a first catheter through said patent blood vessel portion into said occluded blood vessel portion, said first catheter having a distal end portion and a port located proximally of said distal end portion;
(b) extending a second catheter through said first catheter so that a working portion of said second catheter is located in the occluded blood vessel portion;
(c) blocking the occluded blood vessel portion distally of said working portion of said second catheter;
(d) using said second catheter to open a lumen in the occluded portion of the blood vessel for the freer flow of blood therethrough;
(e) introducing an infusate into said occluded blood vessel portion and withdrawing said infusate and any debris produced by the opening of the occluded portion of the blood vessel through a passageway in said first catheter, wherein said infusate comprises therapy means; and
(f) providing a path for blood from the patent blood vessel portion to flow through said port into said passageway for merger with said infusate and debris.

74. The method of claim 73 wherein said therapy means comprises a drug, pharmaceutical, a biologically active material, or microspheres carrying chemicals.

75. the method of claim 74 wherein said biologically active material comprises a growth factor.

76. The method of claim 74 wherein said drug comprises heparin or urokinase

77. The method of claim 73 additionally comprising the step of:
(g) introducing a third catheter through said first catheter, said third catheter being arranged to carry a stent into the lumen formed in the occluded blood vessel to hold said lumen open.

78. The method of claim 73 additionally comprising the steps of:
(g) extending a third catheter through said first catheter, said third catheter being arranged for introducing said infusate into said occluded blood vessel portion.

79. A method for treating a lumen in a portion of a blood vessel of a living being's vascular system, the blood vessel being occluded by an occlusive material, the blood vessel being located distally of a patent blood vessel, said method. comprising:
(a) extending a first catheter through said patent blood vessel portion into said occluded blood vessel portion, said first catheter having a distal end portion and a port located proximally of said distal end portion;
(b) blocking the flow of blood and debris distally of a working head;
(c) providing a vessel-opening catheter having said working head and extending said vessel-opening catheter through said first catheter so that said working bead is located in the occluded blond vessel portion, said first catheter and said vessel-opening catheter defining a passageway therebetween;
(d) operating said working head to open the occluded blood vessel portion for the freer flow of blood therethrough;
(e) introducing an infusate at a first flow rate adjacent said working bead and withdrawing said infusate at a second and higher flow rate to create a differential flow adjacent said working head, whereupon blocked debris is withdrawn with said infusate for passage proximally through said passageway wherein said infusate comprises therapy means; and
(f) providing a path for blood within said patent blood vessel portion to flow into said passageway for merger with said infusate and debris.

80. The method of claim 79 wherein said therapy means comprises a drug, pharmaceutical, a biologically active material, or microspheres carrying chemicals.

81. The method of claim 80 wherein said biologically active material comprises a growth factor.

82. The method of claim 80 wherein said drug comprises heparin or urokinase.

83. A method for treating a lumen in a portion of a blood vessel of a living beings vascular system., the blood vessel being occluded by an occlusive material, the occluded blood vessel being located distally of a patent blood vessel portion, said method comprising:
(a) extending a guide catheter through said patent blood vessel portion into said occluded blood vessel portion;
(b) extending a lumen-opening catheter having a working head through said guide catheter so that said working head is located in the lumen in the occluded blood vessel portion, said guide catheter and said lumen-opening catheter defining a fluid-flow passageway therebetween;
(c) blocking the flow of blood and any debris created distally of said working head;
(d) operating said working head to open the lumen for the freer flow of blood therethrough, wherein, said operation comprises introducing an infusate at a first flow rate at said working head and withdrawing said infusate at a second and higher flow rate to create a differential flow at said working head, whereupon debris is withdrawn with said infusate for passage proximally through said fluid-flow passageway, wherein said infusate comprises therapy means; and
(e) providing a path for blood within the patent blood vessel portion to flow into said fluid-flow passageway for merger with said infusate and the debris.

84. The method of claim 83 wherein said therapy comprises a drug, pharmaceutical, a biologically active material, or microspheres carrying chemicals.

85. The method of claim 84 wherein said biologically active material comprises a growth factor.

86. The method of claim 84 wherein said drug comprises heparin or urokinase.

87. The method of claim 83 wherein said working head is arranged to introduce said infusate liquid in the form of liquid jets.

* * * * *